(12) United States Patent
Schechter

(10) Patent No.: US 6,955,890 B2
(45) Date of Patent: Oct. 18, 2005

(54) METHOD FOR THE IDENTIFICATION AND TREATMENT OF PATHOGENIC MICROORGANISMS INFECTIONS BY INHIBITING ONE OR MORE ENZYMES IN AN ESSENTIAL METABOLIC PATHWAY

(75) Inventor: Alan M. Schechter, Long Beach, CA (US)

(73) Assignee: Pyro Pharmaceuticals, Inc., Long Beach, CA (US)

( * ) Notice: Subject to any disclaimer, the term of this patent is extended or adjusted under 35 U.S.C. 154(b) by 0 days.

(21) Appl. No.: 10/143,128

(22) Filed: May 10, 2002

(65) Prior Publication Data

US 2003/0180830 A1 Sep. 25, 2003

Related U.S. Application Data

(60) Provisional application No. 60/357,222, filed on Feb. 14, 2002, provisional application No. 60/372,459, filed on Apr. 11, 2002, provisional application No. 60/371,670, filed on Apr. 10, 2002, provisional application No. 60/368,738, filed on Mar. 27, 2002, provisional application No. 60/368,614, filed on Mar. 27, 2002, provisional application No. 60/372,478, filed on Apr. 15, 2002, and provisional application No. 60/372,307, filed on Apr. 12, 2002.

(51) Int. Cl.$^7$ ............................ C12Q 1/18; C12Q 1/02; C12N 1/20
(52) U.S. Cl. ........................ 435/32; 435/29; 435/252.3; 435/254.1; 435/254.11; 435/435; 435/254.22; 435/257.2; 435/258.2; 435/258.3; 935/52
(58) Field of Search ................. 435/32, 29, 252.3, 435/254.1, 254.11, 254.22, 257.2, 258.1, 258.2, 258.3; 935/52

(56) References Cited

U.S. PATENT DOCUMENTS

| | | | |
|---|---|---|---|
| 5,614,551 A | * | 3/1997 | Dick et al. .................. 514/454 |
| 5,891,621 A | | 4/1999 | Chabin et al. ................. 435/4 |
| 6,228,588 B1 | | 5/2001 | Benton et al. ................. 435/6 |
| 6,566,048 B1 | * | 5/2003 | Dixon et al. ................... 435/4 |
| 2003/0180830 A1 | * | 9/2003 | Schechter .................... 435/32 |
| 2004/0006040 A1 | * | 1/2004 | Schechter .................... 514/45 |

FOREIGN PATENT DOCUMENTS

GB  WO 99/32635  *  7/1999

OTHER PUBLICATIONS

Goryshin, Igor Yu et al.; "Tn5 in Vitro Transposition" The Journal of Biological Chemistry vol. 273, No. 13, Mar. 27, 1998 pp. 7367–7374.
Bonafonte, M. Angeles et al.; "The relationship between glycogen synthesis.." FEMS Microbiology; Letters 191 (2000) 31–36.
Jackson, Debra W. et al.; "Biofilm Formation and Dispersal. ." Journal of Bacteriology, Jan. 2002, pp 290–301.
Cushman, Mark et al.; "Design Synthesis, and Biological Evaluation. ." J. Org. Chem. 1999, 64, 3838–3845.
Cushman, Mark et al.; "Design and Synthesis of 6–(6–D–RIBITYLAMINO–2, 4–DIHYDROXYPYRIMIDIN–5–YL) . ." Bioorganic & Medicinal Chemistry Letters 9 (1999) 39–42.
"EZ: :TN Transposase" Cat. No. TNP92110, www.epicentre.com.
EZ: :TN <KAN–2> Tnp Transposome Kit Cat No. TSM99K2, www.epicentre.com.
U.S. Appl. No. 10/055,749, Meyer, filed Jan. 22, 2002.

* cited by examiner

*Primary Examiner*—Lousie N. Leary
(74) *Attorney, Agent, or Firm*—Daniel M. Chambeo; BioTechnology Law Group

(57) ABSTRACT

A method for the identification and treatment of pathogenic microorganism infections by inhibiting one or more enzymes in a metabolic pathway by inhibiting the conversion of substrate to produce the penultimate or ultimate product particularly by inhibiting the activity of one or more of the enzymes in the pathway

13 Claims, No Drawings

METHOD FOR THE IDENTIFICATION AND TREATMENT OF PATHOGENIC MICROORGANISMS INFECTIONS BY INHIBITING ONE OR MORE ENZYMES IN AN ESSENTIAL METABOLIC PATHWAY

This application claims benefit of Provisional Application Nos. 60/357,222 filed Feb. 14, 2002, 60/372,459 filed Apr. 11, 2002; 60/371,670 filed Apr. 10, 2002; 60/368,738 filed Mar. 27, 2002; 60/368,614 filed Mar. 27, 2002; 60/372,478 filed Apr. 15, 2002 and 60/372,307 filed Apr. 12, 2002.

FIELD OF THE INVENTION

The present invention is directed to a method for identifying bacterial enzymes that are useful as targets for antibiotic therapy, for identifying compounds useful for such antibiotic therapy and the treatment of microorganism infections by inhibiting enzymes involved in essential metabolic pathways.

BACKGROUND OF THE INVENTION

Biochemical pathways govern the synthesis and metabolism of molecules required by all living organisms. Blocking a metabolic pathway by inhibiting one or more enzymes in a pathway can sometimes cause deleterious consequences for that organism, or a particular affliction, such as an inborn error in metabolism, or death. The inhibition of a pathway that ultimately results in the death of the organism is, a priori, inhibition of a pathway required for the survival of the organism and is termed an essential pathway. The inhibition of a pathway that does not result in the death of the organism can render that organism avirulent by affecting one or more processes that are required for pathogenesis.

Research has identified and analyzed many of the biochemical pathways in various organisms, and many of those results are available in computer databases. Advances in genetic engineering have also identified many of the genes responsible for coding for many of the components in those pathways.

Some biochemical pathways are identical from organism to organism. In other cases, mammals utilize a different pathway from pathogenic organisms for the same or similar purpose. The present inventor has realized that these distinctions can be used to develop a method for the rational design of drugs, specifically of antibiotics. Identifying metabolic pathways that are unique and essential to pathogenic microorganisms can be used as a method to develop novel therapeutics against these pathogenic species without causing harm to the mammalian organism.

Specifically, the identification of an essential metabolic pathway of pathogenic microorganism that is not common to humans can be used as a unique target to develop therapeutics that will inhibit one or more enzymes in that essential pathway. Inhibition of the enzyme by a therapeutic will cause the pathogenic microorganism to die or become avirulent without affecting the mammalian host. Thus, specific inhibitors are unlikely to interfere with human metabolism as humans do not posses the corresponding enzymes.

The method for the identification and treatment of pathogenic microorganism infections by inhibiting one or more enzymes in a metabolic pathway is composed of three general steps:

1. Identifying an essential metabolic pathway found only in a pathogenic organism, but not found in mammals. More specifically, identifying a specific enzyme within an essential metabolic pathway that is essential for the viability and/or virulence (infectivity) of a microorganism but which is not found in mammals.
2. Determining and confirming that the enzyme(s) of an essential metabolic pathway is/are valid targets for therapeutics against pathogenic microorganisms.
3. Screening for and identifying putative inhibitors of one or more specific enzymes within an essential metabolic pathway that interferes with and is essential for the viability and/or virulence (infectivity) of a microorganism but which are not found in mammals.

SUMMARY OF THE INVENTION

The present inventor has determined that it is possible to identify an essential metabolic pathway that interferes with and is essential for the viability and/or virulence (infectivity) of a microorganism but which is not found in mammals, and utilize this distincion for rational drug design for compounds that interfere with that enzyme pathway (site-specific inhibition/targeting).

Moreover, the present inventor has determined that it is possible to identify one or more specific enzymes within an essential metabolic pathway that is/are essential for the viability and/or virulence (infectivity) of a microorganism but which is not found in mammals.

The present inventor has determined that, since the synthesis and metabolism of enzymes within certain pathways are critical to viability of pathogenic microorganisms, namely bacteria, protists, yeast, and fungi, the inhibition of such pathways in bacteria, protists, yeast, and fungi provide a novel class of antibiotics for the treatment of bacterial, protist, yeast, and fungal infections whereas current antibiotics are characterized by inhibition of RNA synthesis, protein synthesis, DNA synthesis and cell wall synthesis, this novel class of antibiotics is characterized by inhibition of more or more enzymes in an essential metabolic pathway.

The inventor has particularly noted that production of the penultimate and/or ultimate molecule in the pathway, is critical to viability of bacteria, protists, yeast, and fungi and since one or more of the enzymes are not present in mammals, the enzymes provide an excellent target for inhibition of bacterial, protist, yeast, and fungal growth, thereby providing a means for inhibiting the growth of microorganisms, or rendering them avirulent, and treating bacterial, protist, yeast, and fugal infections.

The inventor has determined that one or more of the enzymes in an essential metabolic pathway is a unique target to which therapeutics against pathogenic microorganisms, namely bacteria, protists, yeast, and fungi can be site-specifically directed.

A further aspect of the invention is to provide a method of identifying a compound capable of inhibiting the growth of pathogenic microorganisms, or rendering them avirulent, namely bacteria, protists, yeast, and fungi which comprises identifying a compound which inhibits an enzyme important in an essential metabolic pathway, particularly a compound that inhibits the activity of any of the enzymes in the pathway.

Yet another aspect of the invention is to provide a method of identifying a compound capable of inhibiting the growth of pathogenic microorganisms, or rendering them avirulent, namely bacteria, protists, yeast, and fungi which comprises identifying a compound which is an analogue of the substrate, in either the forward or reverse direction in an essential metabolic pathway, particularly a compound that inhibits the activity of any of the enzymes in the pathway by preventing the binding of the enzyme to the substrate.

Another aspect of the invention is to provide a method for treating a microorganism, or rendering them avirulent, namely bacteria, protists, yeast, and fungal infections by administering an effective amount of a compound capable of inhibiting the activity of any of the enzymes in the pathway.

DETAILED DESCRIPTION OF THE INVENTION

Identification of potential new antibiotics has traditionally been accomplished by screening compounds against cultures of the microorganisms of interest. Such screening procedures may test candidate compounds selected because of their structural similarity to known antibiotics or because of other experimental observations that suggest possible activity. But in either event, this type of screening often times requires many cumbersome experiments in order to identify potential candidate compounds. A more rationale approach to drug design and development would more quickly focus on candidate compounds that affect critical targets of the pathogenic microorganism of interest. In other words, instead of blindly screening compounds for possible activity, a rational approach would first identity targets, that if properly inhibited, would adversely affect the viabiltiy or infectivity of pathogenic microbes.

The present inventor has first developed such a rationale drug design approach that more quickly and efficiently focuses drug screening on specific identified targets which are critical and important to viability and infectivity of pathogenic microorganisms. The method of the invention, therefore, comprises:

a) identifying a metabolic pathway in a pathogenic microorganism that is essential to the viability or infectivity of said microorganism;

b) identifying an enzyme in said pathway which enzyme is not present in mammals;

c) confirming that said enzyme is a valid target for affecting the viability or infectivity of said microorganism; and d) identifying a compound that inhibits said enzyme.

1. Identifying an Essential Metabolic Pathway

The first step in the present method is the identification of an essential metabolic pathway in the pathogenic microorganism of interest. Effective treatment of bacterial infections typically means adversely affecting the viability of the bacteria. But for some situations, treatment of bacterial infections can also be accomplished by use of an agent that inhibits the infectivity of the bacteria. The term infecting as used herein includes the ability of an organism to be pathogenic, virulent, pyrogenic or capable of causing disease in a host. Thus, in the present invention, an "essential metabolic pathway" is one which a pathogenic bacteria requires for viability and/or infectivity, such that, inhibition of that pathway adversely affects the infectivity and/or viability of that bacteria in a host.

Many biochemical or metabolic pathways have been analyzed and described for various organisms, including various microorganisms and humans. These descriptions include identification of the various components in the pathway, including starting, intermediate and final products, and necessary enzymes and other reaction components. Various sources are known for descriptions of these pathways, and many are now viewable and searchable via the internet. One exemplary data base is located at http://www.ebi.ac.uk/parasites/TbGN/Proteome/WWW/MAP00950.shtml. This database has three pull-down menu categories from which one can select: (1) classes; (2) classifications; and (3) pathways. For the identification of target enzymes in metabolic pathways, the third auto-menu (pathways) is the most relevant. Within the pathways category, one can pull-down the auto-menu and select the pathway of interest. Once selected, the screen will show access to pathway diagrams (KEGG). Accessing the pathway diagrams takes one to a reference pathway of the metabolic pathway of interest. Within this screen, there is another pull-down menu that lists the various organisms in which this pathway has been elucidated and posted. An organism of interest can be selected and the pathway portrayed.

Functional enzymes, identified by their "Enzyme Classification" (EC) number, as determined by the *International Union of Biochemistry and Molecular Biology*, in a given pathway in a given organism are shown by a selectable green box. Selecting this green box shows another site that provides extensive information on that enzyme. Non-functional enzymes, as identified by their "Enzyme Classification" (EC) number, as determined by the *International Union of Biochemistry and Molecular Biology*, in a given pathway in a given organism are shown by a non-selectable white box.

Comparison of enzymes, by overlay or the like, within pathways amongst a multitude of organisms, especially including humans, can elucidate those enzymes that appear in pathogenic microorganisms of interest and do not appear in humans. Enzymes that appear in pathogenic microorganisms and do not appear in humans that are found in an essential (required for survival or other required functions) metabolic pathway are targets for inhibitors.

According to the present invention, the metabolic pathways of a pathogenic bacteria are analyzed to identify those that are essential. For example, bacteria, and other living organisms, require energy for viability. Pathways involved in energy storage and utilization are, therefore, essential pathways suitable as potential therapeutic targets. But it will be recognized that those skilled in the art will be able to identify other essential pathways required for bacterial viability and infectivity.

2. Identifying a Target Enzyme in the Essential Metabolic Pathway

Once an essential pathway is identified, a comparison of that pathway in the bacteria is then made to the host of interest, such as mammals, particularly humans. If it is found that the pathway is not present in the host of interest, then various components of the pathway are potential therapeutic targets because those targets are absent in the host of interest and inhibition of the target would have no deleterious affect on the host. In other situations, an essential bacteria pathway may have a corresponding pathway in the host of interest, but one or more components of the host pathway are found to be different than the corresponding bacterial components.

In one embodiment of the invention, the potential therapeutic target is an enzyme required for one step in the essential metabolic pathway. Inhibition of that enzyme would then inhibit the pathway, inhibit production of a required end product and thereby inhibit viability or infectivity. In the situation where the essential pathway is missing in the host of interest, more than one enzyme can be a potential therapeutic target. Inhibitor(s) of those enzymes are then, according to the present invention, potential therapeutic agents.

In some situations, the same or very similar metabolic pathway may be found both in the pathogenic bacteria and in the host of interest, but one or more enzyme components in the pathway are different. For example, the pathway (namely the starting, intermediate and final product compounds) may be similar, but the enzyme in the pathogenic bacteria is structurally different than the "corresponding" enzyme in the host of interest. The enzymes may be, for example, analogues of each other. In such a situation, the enzyme can still be a therapeutic target by use of an agent which selectively inhibits only the bacterial enzyme and not the enzyme in the host of interest.

3. Confirming that an Enzyme is a Valid Therapeutic Target

As noted above, a useful therapeutic target is a target, the inhibition of which adversely affects the viability and/or infectivity of the pathogenic bacteria. Analysis of the usefulness of the potential target can be made by treating cultures of the bacteria with candidate compounds and assessing the viability and infectivity of the treated bacteria. But if the thus treated bacteria are not adversely affected, it cannot easily be determined if this is because the target is not essential to the bacteria, or because the candidate compound was unable to act on the target due to delivery or similar causes. Validation of the target according to the rational approach of the present invention is first and more efficiently and conclusively accomplished by use of genetic engineering techniques. In particular, a mutant of the bacteria of interest (a so-called "knock-out") is produced wherein the gene for the enzyme target has been modified so that the bacteria is unable to produce the target enzyme with it's enzymatic activity. This may be accomplished by causing a mutation of the gene, such as a deletion, substitution or insertion mutant, whereby the gene is either incapable of coding for the target enzyme, or codes for a mutated enzyme which does not have the activity of the natural enzyme. Knock-outs may also be created wherein the entire gene for the target enzyme has been deleted. In either case, the knock-out is deficient in the enzymatic activity of interest.

Procedures for making genetic knock-outs are per se known to those skilled in the art, and are described for example, in Akerley, B. J., Rubin, E. J., Camilli, A., Lampe, D. J., Robertson, H. M., and J. J. Mekalanos. Systematic Identification of Essential Genes by in vitro mariner Mutagenesis. (1998) *Proc. Natl. Acad. Sci. USA*. 95:8927–8932.

The thus produced knock-out strain is then cultured under conditions sufficient for viability of the wild-type bacteria. Results that indicate non-viability and/or non-infectivity of the knock-out strain confirm that the tested enzyme is a valid target for screening for a useful antibiotic against the pathogenic bacteria.

4. Identifying a Compound that Inhibits the Target Enzyme

Once an enzyme has been confirmed to be a valid target, candidate compounds are then tested for activity for inhibiting that enzyme. Various in vitro experiments are known to those skilled in the art for measuring the enzyme inhibitory effect of a given compound against a given enzyme. Examples of such procedures are described below.

After a candidate inhibitor compound is shown to be active in vitro against the validated target enzyme, standard and known bacteria and animal in vivo and ex vivo experiments are conducted to measure the activity of the inhibitor.

Inhibitors are compounds that will act on the enzyme, the substrate, or the enzyme-substrate complex to block the functioning of that enzyme to prevent the reaction catalyzed by that enzyme from allowing either or both the forward or reverse reaction from taking place. Inhibitors to enzymes typically disrupt or change one of the functional moieties on the enzyme. Inhibitors of the substrate are typically structural analogues of the substrate such the regulatory or allosteric site of the enzyme does not recognize the substrate. Similarly, inhibitors that affect the enzyme-substrate complex typically affect the conformational state such that binding cannot occur.

Inhibition of one or more enzymes in an essential metabolic pathway will cause the pathogenic microorganism to be non-viable and/or non-infective/pathogenic. The use of that inhibitor compound to treat infection (disease) caused by a pathogenic microorganism becomes an antibiotic or chemotherapeutic. Antibiotics and chemotherapeutics are used to therapeutically treat infection (disease) caused by a pathogenic microorganism.

An antibiotic is an antimicrobial agent produced by microorganisms that kills or inhibits the growth of microorganisms. A chemotherapeutic is an antimicrobial agent of synthetic origin. Agents which kill cells are called cidal agents; agents which inhibit the growth of cells (without killing them) are referred to as static agents. Thus the term bactericidal refers to killing bacteria and bacteriostatic refers to inhibiting the growth of bacterial cells. Bacteriostatic agents render pathogenic microorganisms non-infective/pathogenic. Agents that inhibit enzymes in metabolic pathways can be either bactericidal or bacteriostatic.

The mode of action of most antimicrobials is either inhibitors of DNA, RNA, protein, or cell wall synthesis. Antimicrobials that inhibit enzymes in metabolic pathways represent a novel class of antibiotics. The mechanism of action is the inhibition of an essential process in pathogenic microorganisms, but not found in mammals, such that the inability to produce a required intermediate or end-product within the pathway affects the viability of the pathogenic microorganism or its infectivity/virulence.

In some manner, the depleted intermediate or end-product, is required for bacterial survival or severely impairs the pathogenic microorganism's ability to function normally by rendering (1) the pathogenic microorganism susceptible to the action of the human immune system, and/or (2) non-infective/avirulent. Severely impairing the pathogenic microorganism's ability to function normally by rendering the pathogenic microorganism susceptible to the action of the human immune system can cause either a bactericidal or a bacteriostatic result. Thus, the action of the therapeutic antimicrobial, in this mechanism is not direct, but indirect.

As is well known, antibiotics are currently used to treat a wide range of bacterial and fungal infections, ranging from minor to life threatening infections. Broad spectrum antibiotics treat a variety of gram-positive and gram-negative bacteria, protist, yeast, and fungal organisms, while mild spectrum antibiotics only cover limited types of bacterial, protist, yeast, and fungal organisms and are useful for curing infections with known bacterial, protist, yeast, and fungal strains.

But it has recently been noted that pathogenic bacteria and fungi increasingly exhibit resistance to existing classes of antibiotics, such as penicillin, vancomycin and erythromycin. According to the Center for Disease Control, pathogenic resistance has significantly increased mortality rates, making infectious disease the third largest cause of death in the United States. The rates of antibiotic resistant bacteria have particularly increased recently with respect to *S. aureus*, *Enterococcus* strains, *S. pneumoniae* and *tuberculosis*.

The mechanism of action for most antibiotics is the inhibition of bacterial cell wall completion, or DNA or protein synthesis. Sulfonamides and trimethoprin act by inhibiting an essential metabolic step, namely folate synthesis. But there is a great need for new antibiotics with different targets, especially in light of the ever increasing problem of resistant strains.

The present inventor has found that compounds which act as inhibitors of any of the enzymes in the pathway, offer another class of antibiotics which inhibit an essential step, namely a pathway essential for bacterial, protist, yeast, and fungal biosynthesis and metabolism.

According to the present invention, the present inventor has specifically identified one or more of the enzymes in an essential pathway as an enzyme present in an important biosynthetic or metabolic pathway for pathogenic microorganisms, but absent in mammals, specifically absent in humans. Since the biosynthetic pathway is important for biosynthesis or metabolism in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic bacterial, protist, yeast, and fungal microorganisms which require one or more of the enzymes in an essential pathway, including but not limited to *Yersinia pestis, Pseudomonas aeruginosa, Neisseria meningitides* serogroup A and B, *Helicobacter pylori, Chlamydia trachomatis, Chlamydia pneumoniae, Streptococcus pneumoniae, Haemophilus influenzae, Mycobacterium leprae, Mycobacterium tuberculosis, Vibrio cholerae, Staphylococcus aureus, Giardia lamblia, Entamoeba histolytica, Trichomonas vaginalis, Leishmania donovani, Trypannosome cruzi, Candida albicans*, and *Falciparum plasmodium*.

The above listed bacteria comprise some of the most important pathogenic microorganisms which account for significant numbers of disease patients in the United States and around the world. The following table summarizes the prevalence and current treatments available for these pathogenic microorganisms.

TABLE 1

Prevalence and Current Treatments

| Microorganism | Disease(s) | Incidence (estimated number of new cases/yr) | Prevelence (estimated number of people currently infected) | Treatment |
|---|---|---|---|---|
| *Chlamydia pneumoniae* | Acute and chronic respiratory diseases including: pneumonia, pharyngitis, bronchitis, sinusitis, otitis media, COPD, asthma, Reiter syndrome, and sarciodosis. | | | |
| *Chlamydia trachomatis* | STD and blindness (tracoma). | 3 million/yr STD | 89 million/yr STD; 400 million partially blind, 6 million totally blind. | Doxycycline, tetracycline, chloramphenicol, refampicin, fluoroquinones, erythromycin, and azithromycin |
| *Escherichia coli* O157 (food poisoning) | Abdominal cramps, non-bloody diarrhea, hemorrhagic colitis, and haemolytic-uraemic syndrome. | | | |
| *Haemophilus influenzae* | Bacteremia, acute bacterial meningitis, otitis media, sinusitis, and pneumonia. | 3.5 million/yr | | Ampicillin, cephalosporin, chloramphenicol, tetracycline, sulfa drugs, and amoxicillin |
| *Mycobacterium leprae* | Leprosy (Hansen's disease) | 250 new cases/yr in the U.S., 600,000 new cases/yr world-wide. | 12 million world-wide. It is a public health problem in 72 countries, 19 of which account for 90% of all the cases in the world. | Dapsone, refampin, ethionamide |
| *Mycobacterium tuberculosis* | Tuberculosis | >20,000 in the U.S. | 16 million world-wide. According to the WHO, tuberculosis is the number one killer among infectious diseases in the world. TB kills more people than AIDS, malaria, and | Isoniazid, rifampin, ethambutol, and pyrazinamide. |

TABLE 1-continued

Prevalence and Current Treatments

| Microorganism | Disease(s) | Incidence (estimated number of new cases/yr) | Prevelence (estimated number of people currently infected) | Treatment |
| --- | --- | --- | --- | --- |
| | | | tropical diseases combined. | |
| Salmonella typhimurium | Salmonellosis, abdominal cramps, non-bloody diarrhea. | >50,000/yr world-wide | | Ampicillin, chloramphenicol, streptomycin, sulphonamides, and tetracycline |
| Vibrio cholerae | Cholera | >50,000/yr; mostly in southeast asia. | Over 1,000,000 reported cases throughout the world. Usually epidemic or pandemic. | |

Description of Method for Inhibition Screening

As noted above, one aspect of the present invention is a method for the identification of a compound capable of inhibiting the growth of pathogenic microorganisms by interfering with the activity of any of the enzymes in the pathway. Compounds can be identified by incubating a sample of bacteria in a solution containing a known amount of substrate in the presence or absence of a test compound, assessing the effect on conversion of any of the enzymes in the pathway, wherein, a lower level of conversion in the presence of the test compound, compared with the level of conversion in the absence of the test compound, indicates that the test compound inhibits the activity of the enzyme.

Compounds capable of inhibiting any of the enzymes in the pathway can also be identified by means of in vitro experiments by exposing a substrate to a plurality of test compounds and identifying those compounds which inhibit the tested enzyme according to known catalytic measurement techniques.

One particular in vitro method for assessing the activity of an inhibitor to any of the enzymes in the pathway:

Enzyme assays are performed at a subsaturating concentration of substrate (depending on the enzyme, 0.2–1 mM,= 0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 $\mu$M and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

Useful inhibitors can also be identified, and potential inhibitors assessed, by in vitro treatment of bacteria, protest, yeast, and fungi in, for example, culture tubes or petri dish samples. Such assessments can be performed, for example, by the spreading a measured a liquot of a diluted bacteria culture unto nutrient agar plates, both treated and control, and counting the number of visible cells. Detailed procedures are well known to those skilled in the art as shown for example in Miller, *Experiments in Molecular Genetics*, Cold Spring Harbor Laboratory, 1992.

Compounds which inhibit any of the enzymes in the pathway can also be assessed in an animal model, an in vivo test. Such tests can be conducted in an animal which is susceptible to infection by the pathogenic microorganism of interest. In vivo animal model assessments can be conducted, for example, by procedures such as those described in U.S. Pat. No. 5,871,951.

The present invention further provides a method for treating pathogenic microorganism infections in a patient by administering to the patient an effective amount of an inhibitor against any of the enzymes in the pathway, wherein an effective amount of the inhibitor will inhibit the activity of the enzyme so as to decrease viability of and/or kill the microorganism or render the microorganism avirulent. The inhibitor utilized in the treatment may be one identified by one of the methods described above, or inhibitors may be identified by any other method.

The following examples describe enzyme targets identified by the method of the present invention.

EXAMPLE 1

Aldolase

1. Description of Relevant Pathway(s)

Glycolysis is the primary pathway for anaerobic degradation of D-glucopyranoses and other D-hexopyranoses. It is probably universal among organisms: certainly the enzymes which catalyze the pathway's reactions are among the most conserved (and therefore presumably most ancient) among proteins. The process is a series of consecutive chemical conversions that require the participation of eleven different enzymes, most of which have been crystallized and thoroughly studied. Glycolysis begins with a single molecule of glucose and concludes with the production of two molecules of pyruvic acid. The pathway is seen to be degradative, or catabolic, in that the six-carbon glucose is reduced to two molecules of the three-carbon pyruvic acid. Much of the energy that is liberated upon degradation of glucose is conserved by the simultaneous formation of the high-energy molecule adenosine triphosphate (ATP). Two reactions of the glycolytic sequence proceed with the concomitant production of ATP, thus ATP synthesis is said to be coupled to glycolysis. Hundreds of cellular reactions, particularly those involved in the synthesis of cellular components and those that allow the cell to perform mechanical work, require the participation of ATP as a source of chemical energy. While glycolysis is the primary fuel process for some organisms that do not require oxygen, such as yeast, aerobic organisms can only gain a small portion of their needed energy from this process.

Glycolysis occurs in two major stages, the first of which is the conversion of the various sugars to a common intermediate, glucose-6-phosphate. The second major phase is the conversion of glucose-6-phosphate to pyruvate. The products of glycolysis are further metabolized to complete the breakdown of glucose. Their ultimate fate varies depending upon the organism. In certain microorganisms lactic acid is the final product produced from pyruvic acid, and the process is referred to as homolactic fermentation. In certain bacteria and in brewer's yeast, lactic acid is not produced in large quantities. Instead pyruvic acid, which is also the precursor of lactic acid, is converted to ethanol and carbon dioxide by an enzyme-catalyzed two-step process, termed alcoholic fermentation. In the tissues of many organisms, including mammals, glycolysis is a prelude to the complex metabolic machinery that ultimately converts pyruvic acid to carbon dioxide and water with the concomitant production of much ATP and the consumption of oxygen.

The following reactions comprise the catabolism of glucose:

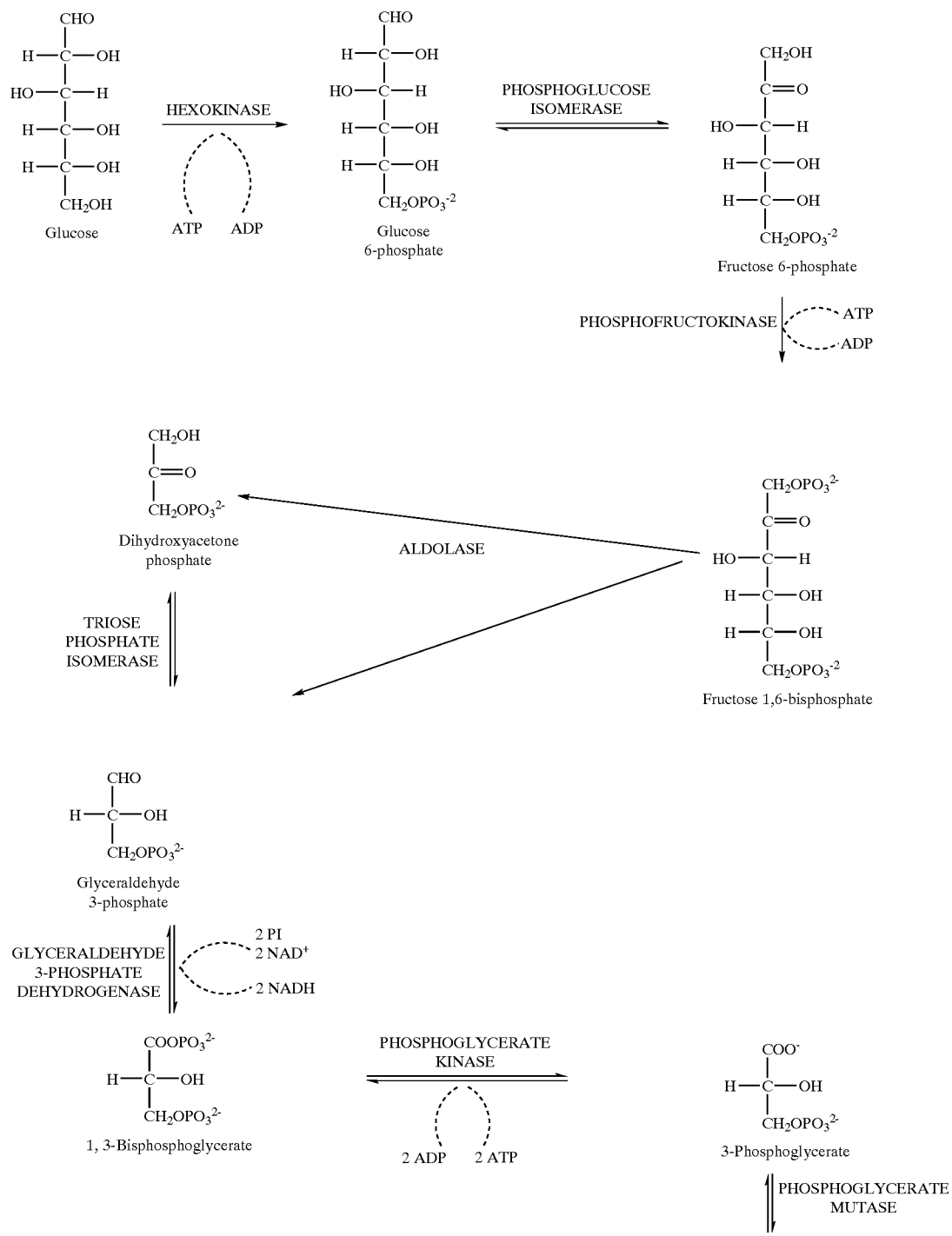

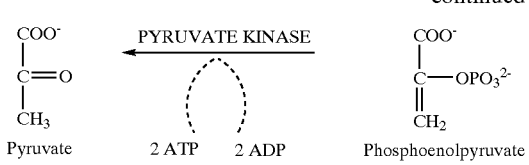
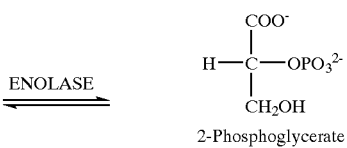

The Individual Reactions of Glycolysis

The pathway of glycolysis can be seen as consisting of 2 separate phases. The first is the chemical priming phase requiring energy in the form of ATP, and the second is considered the energy-yielding phase. In the first phase, 2 equivalents of ATP are used to convert glucose to fructose-1,6-bisphosphate (F-1,6-BP). In the second phase F-1,6-BP is degraded to pyruvate, with the production of 4 equivalents of ATP and 2 equivalents of NADH.

The Hexokinase Reaction

The ATP-dependent phosphorylation of glucose to form glucose-6-phosphate (G6P) is the first reaction of glycolysis, and is catalyzed by tissue-specific isoenzymes known as hexokinases. The phosphorylation accomplishes two goals: First, the hexokinase reaction converts nonionic glucose into an anion that is trapped in the cell, since cells lack transport systems for phosphorylated sugars. Second, the otherwise biologically inert glucose becomes activated into a labile form capable of being further metabolized.

Phosphohexose Isomerase

The second reaction of glycolysis is an isomerization, in which G6P is converted to fructose-6-phosphate (F6P). The enzyme catalyzing this reaction is phosphohexose isomerase (also known as phosphoglucose isomerase). The reaction is freely reversible at normal cellular concentrations of the two hexose phosphates and thus catalyzes this interconversion during glycolytic carbon flow and during gluconeogenesis.

6-Phosphofructo-1-Kinase (Phosphofructokinase-1, PFK-1)

The next reaction of glycolysis involves the utilization of a second ATP to convert F6P to fructose-1,6-bisphosphate (F-1,6-BP). This reaction is catalyzed by 6-phosphofructo-1-kinase, better known as phosphofructokinase-4 or PFK-1. This reaction is not readily reversible because of its large positive free energy ($DG^0$=+5.4 kcal/mol) in the reverse direction. Nevertheless, fructose units readily flow in the reverse (gluconeogenic) direction because of the ubiquitous presence of the hydrolytic enzyme, fructose-1,6-bisphosphatase (F-1,6-BPase).

The presence of these two enzymes in the same cell compartment provides an example of a metabolic futile cycle, which if unregulated would rapidly deplete cell energy stores. However, the activity of these two enzymes is so highly regulated that PFK-1 is considered to be the rate-limiting enzyme of glycolysis and F-1,6-BPase is considered to be the rate-limiting enzyme in gluconeogenesis.

Aldolase

Aldolase catalyses the hydrolysis of F-1,6-BP into two 3-carbon products: dihydroxyacetone phosphate (DHAP) and glyceraldehyde-3-phosphate (G3P). The aldolase reaction proceeds readily in the reverse direction, being utilized for both glycolysis and gluconeogenesis.

Triose Phosphate Isomerase

The two products of the aldolase reaction equilibrate readily in a reaction catalyzed by triose phosphate isomerase. Succeeding reactions of glycolysis utilize G3P as a substrate; thus, the aldolase reaction is pulled in the glycolytic direction by mass action principals.

Glyceraldehyde-3-Phosphate Dehydrogenase

The second phase of glucose catabolism features the energy-yielding glycolytic reactions that produce ATP and NADH. In the first of these reactions, glyceraldehyde-3-P dehydrogenase (G3PDH) catalyzes the $NAD^+$-dependent oxidation of G3P to 1,3-bisphosphoglycerate (1,3-BPG) and NADH. The G3PDH reaction is reversible, and the same enzyme catalyzes the reverse reaction during gluconeogenesis.

Phosphoglycerate Kinase

The high-energy phosphate of 1,3-BPG is used to form ATP and 3-phosphoglycerate (3PG) by the enzyme phosphoglycerate kinase. Note that this is the only reaction of glycolysis or gluconeogenesis that involves ATP and yet is reversible under normal cell conditions. Associated with the phosphoglycerate kinase pathway is an important reaction of erythrocytes, the formation of 2,3-BPG by the enzyme bisphosphoglycerate mutase. 2,3-BPG is an important regulator of hemoglobin's affinity for oxygen. Note that 2,3-bisphosphoglycerate phosphatase degrades 2,3-BPG to 3-phosphoglycerate, a normal intermediate of glycolysis. The 2,3-BPG shunt thus operates with the expenditure of 1 equivalent of ATP per triose passed through the shunt. The process is not reversible under physiological conditions.

Phosphoglycerate Mutase and Enolase

The remaining reactions of glycolysis are aimed at converting the relatively low energy phosphoacyl-ester of 3-PG to a high-energy form and harvesting the phosphate as ATP. The 3-PG is first converted to 2-PG by phosphoglycerate mutase and the 2-PG conversion to phosphoenoylpyruvate (PEP) is catalyzed by enolase Pyruvate Kinase The final reaction of aerobic glycolysis is catalyzed by the highly regulated enzyme pyruvate kinase (PK). In this strongly exergonic reaction, the high-energy phosphate of PEP is conserved as ATP. The loss of phosphate by PEP leads to the production of pyruvate in an unstable enol form, which spontaneously tautomerizes to the more stable, keto form of pyruvate. This reaction contributes a large proportion of the free energy of hydrolysis of PEP.

Regulation of Glycolysis

The reactions catalyzed by hexokinase, PFK-1 and PK all proceed with a relatively large free energy decrease. These nonequilibrium reactions of glycolysis would be ideal candidates for regulation of the flux through glycolysis. In vitro studies have shown all three enzymes to be allosterically controlled.

Regulation of hexokinase, however, is not the major control point in glycolysis. This is due to the fact that large amounts of G6P are derived from the breakdown of glycogen (the predominant mechanism of carbohydrate entry into glycolysis in skeletal muscle) and, therefore, the hexokinase reaction is not necessary. Regulation of PK is important for reversing glycolysis when ATP is high in order to activate gluconeogenesis. As such this enzyme catalyzed reaction is not a major control point in glycolysis. The rate limiting step in glycolysis is the reaction catalyzed by PFK-1.

PFK-1 is a tetrameric enzyme that exist in two conformational states termed R and T that are in equilibrium. ATP is both a substrate and an allosteric inhibitor of PFK-1. Each subunit has two ATP binding sites, a substrate site and an inhibitor site. The substrate site binds ATP equally well when the tetramer is in either conformation. The inhibitor site binds ATP essentially only when the enzyme is in the T state. F6P is the other substrate for PFK-1 and it also binds preferentially to the R state enzyme. At high concentrations of ATP, the inhibitor site becomes occupied and shifting the equilibrium of PFK-1 conformation to that of the T state decreasing PFK-1's ability to bind F6P. The inhibition of PFK-1 by ATP is overcome by AMP which binds to the R state of the enzyme and, therefore, stabilizes the conformation of the enzyme capable of binding F6P. The most important allosteric regulator of both glycolysis and gluconeogenesis is fructose-2,6-bisphosphate, F-2,6-BP, which is not an intermediate in glycolysis or in gluconeogenesis.

The synthesis of F-2,6-BP is catalyzed by the bifunctional enzyme PFK-2/F-2,6-BPase. In the nonphosphorylated form the enzyme is known as PFK-2 and serves to catalyze the synthesis of F-2,6-BP. The result is that the activity of PFK-1 is greatly stimulated and the activity of F-1,6-BPase is greatly inhibited.

Under conditions where PFK-2 is active, fructose flow through the PFK-1/F-1,6-BPase reactions takes place in the glycolytic direction, with a net production of F-1,6-BP. When the bifunctional enzyme is phosphorylated it no longer exhibits kinase activity, but a new active site hydrolyzes F-2,6-BP to F6P and inorganic phosphate. The metabolic result of the phosphorylation of the bifunctional enzyme is that allosteric stimulation of PFK-1 ceases, allosteric inhibition of F-1,6-BPase is eliminated, and net flow of fructose through these two enzymes is gluconeogenic, producing F6P and eventually glucose.

Fructose 1,6-bisphosphate (FBP) aldolase (more commonly referred to as aldolase and technically known as D-glyceraldehyde-3-phosphate lyase, (EC 4.1.2.13)) is a ubiquitous glycolytic enzyme that catalyzes the reversible cleavage of fructose 1,6-bisphosphate to glyceraldehyde 3-phosphate (G3P) and dihydroxyacetone phosphate (DHAP). The enzyme also catalyzes the cleavage of structurally related sugar phosphates including fructose-1-phosphate (F-1-P), an intermediate of fructose metabolism. Comparative studies of aldolases derived from diverse sources have demonstrated the presence of two classes of FBP aldolase with different catalytic and molecular properties (1); Class I aldolases are found in animals, plants, and green algae while class II aldolases are found in bacteria, yeast, protists, and fungi. Class II enzymes are homodimeric and requires one zinc ion per monomer for catalysis.

The present inventor has determined that, since the catabolism and metabolism of the glycolytic pathway is critical to the viability of bacteria, yeast, protists, and fungi, the inhibition of such pathway in bacteria, yeast, protists, and fungi provides a novel class of antibiotics for the treatment of bacterial, yeast, protist, and fungal infections whereas current antibiotics are characterized by inhibition of protein synthesis, DNA synthesis and cell wall synthesis, this novel class of antibiotics is characterized by inhibition of the glycolytic pathway. The inventor has particularly noted that production of glyceraldehyde-3-phosphate (G3P) and dihydroxyacetone phosphate (DHAP), is critical to the viability of bacteria, yeast, protists, and fungi and since fructose 1,6-bisphosphate (FBP) aldolase, Class II (D-glyceraldehyde-3-phosphate lyase, (EC 4.1.2.13) is not present in mammals, the enzyme provides an excellent target for inhibition of bacterial, yeast, protist, and fungal growth, thereby providing a means for inhibiting the growth of microorganisms and treating bacterial, yeast, protist, and fungal infections.

The present inventor has discovered that while certain important pathogenic microorganisms require the activity of fructose 1,6-bisphosphate (FBP) aldolase, Class II (EC 4.1.2.13) to produce G3P and DHAP, that enzyme is not present in mammals, particularly not in humans. As a result, the present inventor has first determined that inhibition of fructose 1,6-bisphosphate (FBP) aldolase, Class II (EC 4.1.2.13) provides an excellent target for inhibiting the growth of pathogenic microorganisms, while not inhibiting any important biosynthetic pathway in humans.

As noted above, in bacteria, yeast, protist, and fungi, fructose 1,6-bisphosphate (FBP) aldolase, Class II (EC 4.1.2.13) catalyzes the reaction of fructose 1,6-bisphosphate (FBP) to produce G3P and DHAP. In mammals, plants, and green algae, the "corresponding" reaction is catalyzed by fructose 1,6-bisphosphate (FBP) aldolase, Class I.

The class I aldolases of animals and higher plants have been widely studied. The enzymes are invariably tetrameric and both amino acid-sequence and nucleic acid sequences indicate that they are highly conserved and derived by divergent evolution from a common ancestral gene. They have identical molecular weights and subunit structures, readily form mixed hybrids in vivo and in vitro, and catalyze the same overall reactions, albeit with different kinetics.

Three unique forms of class I aldolase have been detected in various tissues of vertebrate species including man. These three enzymes, aldolase A (isolated from muscle), aldolase B (isolated from liver) and aldolase C (isolated from brain) have all been purified to homogeneity from rabbit tissues and have been extensively characterized. It is clear that these isozymes are closely related. They have identical molecular weights, form mixed hybrids in vivo and in vitro, and catalyze the same overall reactions. However, it is also clear that each is a unique protein species. The three forms are immunologically distinct, have different peptide maps, have distinguishable catalytic activities, have different chromosomal locations, and different gene sequences.

In humans, aberrant aldolase activity has been associated with several inborn errors of metabolism. A genetic defect of human aldolase A is associated with hereditary hemolytic anemia. A deficiency in F1P cleavage by aldolase B in the liver, kidney, and small intestine results in a disorder known as hereditary fructose intolerance.

According to the present invention, the present inventor has specifically identified fructose 1,6-bisphosphate (FBP) aldolase, Class II (EC 4.1.2.13) as an enzyme present in an important biosynthetic pathway for pathogenic microorganisms, but absent in mammals, specifically absent in humans. Since the biosynthetic pathway is important for glucose metabolism in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic bacterial, yeast, fungi, and protest microorganisms which require fructose 1,6-bisphosphate (FBP) aldolase, Class II (EC 4.1.2.13), including *Chlamydia pneumoniae, Chlamydia trachomatis, Escherichia coli* O157*, Haemophi-*

*lus influenzae, Mycobacterium leprae, Mycobacterium tuberculosis, Salmonella typhimurium* and *Vibrio cholerae, Streptococcus pneumoniae, Bacillus subtilus, Bacillus anthrax,* and *Staphylococcus aureus, Trypannosome brucei, Leishmania donovani, Giardia lamblia,* and *Entamoeba histolytica, Acinetobacter baumannii, Candida albicans, Gardnerella vaginalis, Bacteroides, Mobiluncus,* and *Mycoplasma hominis.*

2. Description of Method for Inhibition Screening

As noted above, one aspect of the present invention is a method for the identification of a compound capable of inhibiting the growth of pathogenic microorganisms by interfering with the activity of fructose 1,6-bisphosphate (FBP) aldolase, Class II. Compounds can be identified by incubating a sample of bacteria in a solution containing a known amount of fructose 1,6-bisphosphate (FBP) in the presence or absence of a test compound, assessing the effect on conversion of fructose 1,6-bisphosphate (FBP); wherein, a lower level of conversion in the presence of the test compound, compared with the level of conversion in the absence of the test compound, indicates that the test compound inhibits the activity of the enzyme.

Compounds capable of inhibiting fructose 1,6-bisphosphate (FBP) aldolase, Class II can also be identified by means of in vitro experiments by exposing a substrate comprising fructose 1,6-bisphosphate (FBP) to a plurality of test compounds and identifying those compounds which inhibit the tested enzyme according to known catalytic measurement techniques.

One particular in vitro method for assessing the activity of an inhibitor to fructose 1,6-bisphosphate (FBP) aldolase, Class II is the following:

Enzyme assays are performed at a subsaturating concentration of substrate (depending on the enzyme, 0.2–1 mM, fructose 1,6-bisphosphate (FBP)=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 μM and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

Useful inhibitors can also be identified, and potential inhibitors assessed, by in vitro treatment of bacteria, yeast, protest, and fungi in, for example, culture tubes or petri dish samples. Such assessments can be performed, for example, by the above method.

Compounds which inhibit fructose 1,6-bisphosphate (FBP) aldolase, Class II can also be assessed in an animal model, an in vivo test. Such tests can be conducted in an animal which is susceptible to infection by the pathogenic microorganism of interest. In vivo animal model assessments can be conducted, for example, by procedures such as those described in U.S. Pat. No. 5,871,951.

3. Useful Inhibitor(s)

The present invention further provides a method for treating pathogenic microorganism infections in a patient by administering to the patient an effective amount of an inhibitor against fructose 1,6-bisphosphate (FBP) aldolase, Class II, wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method. One such inhibitor is p-glycolohydroxamate (PGH), described by U.S. Pat. No. 5,773,592 to Mills which has the following structure:

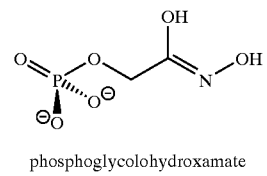

phosphoglycolohydroxamate

PGH can be considered a transition state analogue of DHAP, which also is an inhibitor of

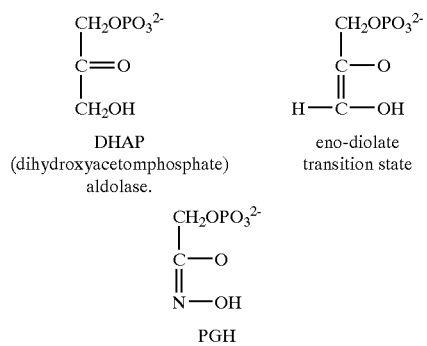

This compound can be prepared as follows:

PGH is synthesized from tri(monocyclohexylammonium) 2-phosphoglycolate (Sigma-Aldrich Chemie GmBH, Germany), which is first converted into the free acid form using Dowex 50W-H$^+$. Treatment of the 2-phosphoglycolic acid with 2,2-dimethoxypropane in methanol yielded the methyl ester 2PG, which is converted to PGH (Collins, K. D. (1974) *J. Biol. Chem.* 249:136–142). Purification of PGH to homogeneity is done on a DEAE Sephadex A-25 column using a 0–0.4 M lithium chloride gradient. Two consecutive purification columns are needed to obtain a product free of 2PG. PGH is isolated from LiCl by precipitation with barium salts (Lewis, D. J. & Lowe, G., (1977) Eu.r.J. Biochem. October, 17;80(1):119–33). The purity of the barium salt of PGH was confirmed by P NMR and H NMR and mass spectrometry. PGH solutions are prepared as described (Lewis & Lowe, 1977), and the concentration of dissolved PGH is determined spectrophotometrically (Collins, 1974).

EXAMPLE 2

Coenzyme A(CoA)

1. Description of Relevant Pathway(s)

Coenzyme A (CoA) is an essential coenzyme in a variety of reactions that sustain life. CoA is required for chemical reactions that generate energy from food (fat, carbohydrates, and proteins). The synthesis of essential fats, cholesterol, and steroid hormones requires CoA, as does the synthesis of the neurotransmitter, acetylcholine, and the hormone, melatonin. Heme, a component of hemoglobin, requires a CoA-containing compound for its synthesis. Metabolism of a number of drugs and toxins by the liver requires CoA.

Coenzyme A was named for its role in acetylation reactions. Most acetylated proteins in the body have been modified by the addition of an acetate group that was donated by CoA. Protein acetylation affects the 3-dimensional structure of proteins, potentially altering their function. Protein acetylation affects the activity of peptide hormones and appears to play a role in cell division and DNA replication. Protein acetylation also affects gene expression by facilitating the transcription of mRNA. A number of proteins are also modified by the attachment of long-chain fatty acids donated by CoA. These modifications are known as protein acylation, and appear to play a central role in cell signaling.

Pantothenic acid is a component of Coenzyme A. Coenzyme A is a carrier of acyl groups. The structure of CoA contains an adenine nucleotide, pantothenic acid and beta-mercaptoethylamine. The beta-mercaptoethylamine has the reactive thiol group (—SH) which comes from cysteine to which the acyl group binds to. A thiol group bound to an acyl group results in the formation of a thioester bond. Therefore it is the thiol group that carries the acyl group. An example of CoA is with the enzyme pyruvate dehydrogenase:

Pyruvate+NAD+CoA-SH+$H_2O$ via pyruvate dehydrogenase forms acetyl-CoA+$HCO_3^-$+NADH+$H^+$ Pyruvate is decarboxylated by pyruvate dehydrogenase to form acetyl CoA (acetyl group is the acyl group). The acetyl group of acetyl-CoA can then be transferred to oxaloacetate to form citrate and CoA-SH by way of the enzyme citrate synthase. The formation of citrate from oxaloacetate and acetyl-CoA is the first step in the Krebbs cycle.

The acyl-carrier protein requires pantothenic acid in the form of 4'-phosphopantetheine for its activity as an enzyme. Both CoA and the acyl-carrier protein are required for the synthesis of fatty acids. Fatty acids are a component of some lipids, which are fat molecules essential for normal physiological function. Among these essential fats are sphingolipids, which are a component of the myelin sheath that enhances nerve transmission, and phospholipids in cell membranes.

Coenzyme A (CoA), the principal acyl group carrier in all living cells, is required for numerous synthetic and degradative reactions in intermediary metabolism. It is invariably synthesized from pantothenate (vitamin $B_5$), cysteine, and ATP in five steps.

The essential part of the CoA biosynthetic pathway is shown below:

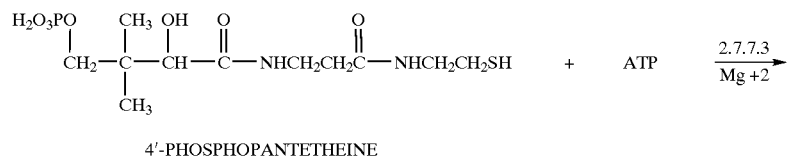

4'-PHOSPHOPANTETHEINE

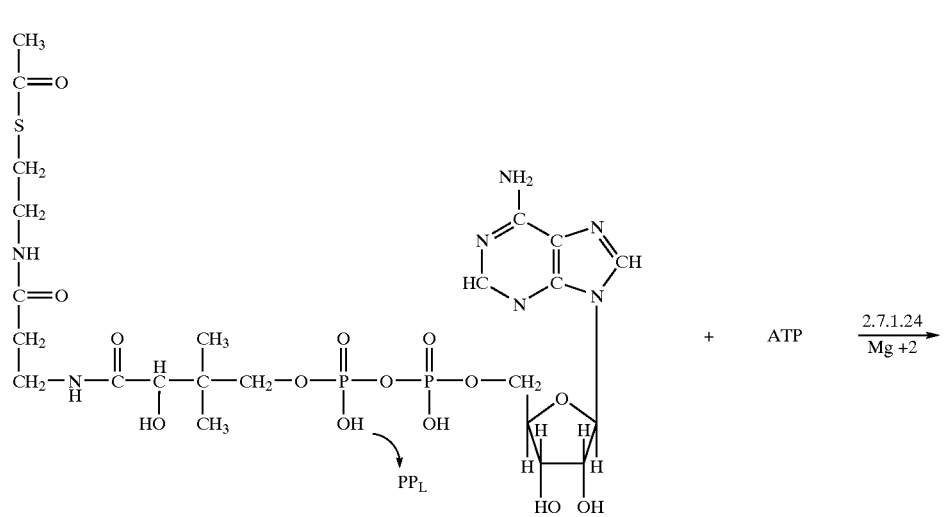

DEPHOSPHO-CoA

-continued

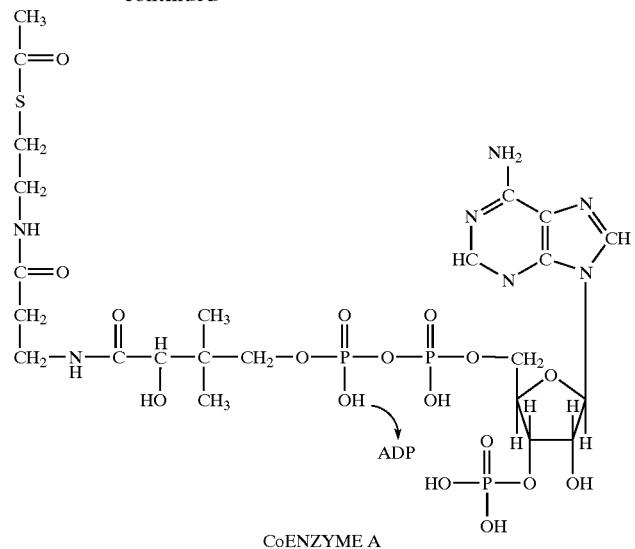

CoENZYME A

The penultimate step is the transfer of an adenylyl group from ATP to 4'-phosphopantetheine, which is catalyzed by phosphopantetheine adenylyltransferase (PPAT, EC 2.7.7.3), to yield dephospho-CoA (dPCoA) and pyrophosphate:
1. ATP+pantetheine 4'-phosphate→dephospho-CoA+PPi Subsequent phosphorylation at the 3'-hydroxyl of the ribose ring by dephospho-CoA kinase (dPCoAK, EC 2.7.1.24) produces the acyl group carrier, CoA.
2. ATP+dephospho-CoA→CoA+ADP PPAT catalyzes the rate-limiting step in the pathway. PPAT is thus a target for inhibition, aimed at reducing the intracellular levels of CoA and preventing bacterial growth. In mammalian systems, PPAT and dPCoAK occur as a bifunctional enzyme complex, leading to the common use of the term "CoA synthase" to describe this complex. In bacteria, however, PPAT and dPCoAK occur as separable enzymes.

U.S. Pat. No. 6,210,890 to Hillman, et. al., describes the discovery of a new human peroxisomal thioesterase and the polynucleotides encoding it satisfies a need in the art by providing new compositions which are useful in the diagnosis, prevention and treatment of cancer, inflammation, and disorders associated with fatty acid metabolism. thioesterases catalyze the chain-terminating step in the de novo biosynthesis of fatty acids. Chain termination involves the hydrolysis of the thioester bond which links the fatty acyl chain to the 4'-phosphopantetheine prosthetic group of the acyl carrier protein (ACP) subunit of the fatty acid synthase. CoA plays an important role in the synthesis and metabolism of fatty acids. Esterification of the fatty acid carboxylic acid group with CoA creates a thioester bond which activates the fatty acid molecule for nucleophilic attack and subsequent metabolic conversions. Likewise, hydrolysis of the fatty acyl-CoA thioester bond renders the fatty acid carboxylate group unreactive toward nucleophilic attack.

The present inventor has determined that, since the biosynthesis of Coenzyme A (CoA) is critical to the viability of bacteria, the inhibition of this pathway in bacteria provides a novel class of antibiotics for the treatment of bacterial infections whereas current antibiotics are characterized by inhibition of protein synthesis, DNA synthesis and cell wall synthesis, this novel class of antibiotics is characterized by inhibition of enzymes in the CoA pathway.

The inventor has particularly noted that production of dephospho-CoA and Coenzyme A (CoA), is critical to the viability of bacteria and since phosphopantetheine adenylyltransferase (PPAT, EC 2.7.7.3) and dephospho-CoA kinase (dPCoAK, EC 2.7.1.24) are not present in mammals, the enzymes provide an excellent target for inhibition of bacterial growth, thereby providing a means for inhibiting the growth of microorganisms and treating bacterial infections. It should be noted that both enzymes are utilized by a representative group of bacteria that include, but are not limited to: *Neisseria meingitidis* serogroup A, *Haemophilus influenzae, Pseudomonas aeruginosa, Staphylococcus aureus, Helicobacter pylori, Streptococcus pyogenes*, and *Mycobacterium tuberculosis*. Furthermore, it should be noted that the enzyme phosphopantetheine adenylyltransferase (PPAT, EC 2.7.7.3) is utilized by a representative group of bacteria that include, but are not limited to: *Neisseria meingitidis* serogroup B and *Yersinia pestis*. These bacteria do not have the enzyme dephospho-CoA kinase (dPCoAK, EC 2.7.1.24). Yet furthermore, it should be noted that the enzyme dephospho-CoA kinase (dPCoAK, EC 2.7.1.24) is utilized by a representative group of bacteria that include, but are not limited to: *Chlamydia trachomatis* and *Streptococcus pneumoniae*. These bacteria do not have the enzyme phosphopantetheine adenylyltransferase (PPAT, EC 2.7.7.3).

The present inventor has discovered that while certain important pathogenic microorganisms require the activity of either or both phosphopantetheine adenylyltransferase (PPAT, EC 2.7.7.3) and dephospho-CoA kinase (dPCoAK, EC 2.7.1.24) to produce CoA, both enzymes are not present in mammals, particularly not in humans. In higher organisms (humans), PPAT and dPCoAK occur as a bifunctional enzyme complex. The enzyme complex is called CoA synthase. As a result, the present inventor has first determined that inhibition of either or both phosphopantetheine adenylyltransferase (PPAT, EC 2.7.7.3) and dephospho-CoA kinase (dPCoAK, EC 2.7.1.24) provides an excellent target for inhibiting the growth of pathogenic microorganisms, while not inhibiting any important biosynthetic pathway in humans.

The present inventor has first recognized the importance of this distinction in providing a target for inhibition of pathogenic microorganisms. As is well known, antibiotics are currently used to treat a wide range of bacterial infections, ranging from minor to life threatening infections. Broad spectrum antibiotics treat a variety of gram-positive and gram-negative organisms, while mild spectrum antibiotics only cover limited types of bacterial organisms and are useful for curing infections with known bacterial strains.

According to the present invention, the present inventor has specifically identified either or both phosphopantetheine adenylyltransferase (PPAT, EC 2.7.7.3) and dephospho-CoA kinase (dPCoAK, EC 2.7.1.24) as enzymes present in an important biosynthetic pathway for pathogenic microorganisms, but absent in mammals, specifically absent in humans. Since the biosynthetic pathway is important for CoA biosynthesis in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic microorganisms which require either or both phosphopantetheine adenylyltransferase (PPAT, EC 2.7.7.3) and dephospho-CoA kinase (dPCoAK, EC 2.7.1.24), including *Neisseria meingitidis* serogroup A, *Haemophilus influenzae, Pseudomonas aeruginosa, Staphylococcus aureus, Helicobacter pylori, Streptococcus pyogenes, Yersinia pestis, Mycobacterium tuberculosis, Neisseria meingitidis* serogroup B, *Chlamydia trachomatis* and *Streptococcus pneumoniae.*

2. Description of Method for Inhibition Screening

As noted above, one aspect of the present invention is a method for the identification of a compound capable of inhibiting the growth of pathogenic microorganisms by interfering with the activity of either or both phosphopantetheine adenylyltransferase (PPAT, EC 2.7.7.3) and dephospho-CoA kinase (dPCoAK, EC 2.7.1.24). Compounds can be identified by incubating a sample of bacteria in a solution containing a known amount of either 4'-phosphopantetheine or dephospho-CoA, respectively, in the presence or absence of a test compound, assessing the effect on conversion of 4'-phosphopantetheine or dephospho-CoA, respectively; wherein, a lower level of conversion in the presence of the test compound, compared with the level of conversion in the absence of the test compound, indicates that the test compound inhibits the activity of the enzyme.

Compounds capable of inhibiting either/or both phosphopantetheine adenylyltransferase (PPAT, EC 2.7.7.3) and dephospho-CoA kinase (dPCoAK, EC 2.7.1.24) can also be identified by means of in vitro experiments by exposing a substrate comprising 4'-phosphopantetheine or dephospho-CoA, respectively, to a plurality of test compounds and identifying those compounds which inhibit the tested enzyme according to known catalytic measurement techniques.

One particular in vitro method for assessing the activity of an inhibitor to either or both phosphopantetheine adenylyltransferase (PPAT, EC 2.7.7.3) and dephospho-CoA kinase (dPCoAK, EC 2.7.1.24) is the following:

Enzyme assays are performed at a subsaturating concentration of substrate (depending on the enzyme, 0.2–1 mM, 4'-phosphopantetheine or dephospho-CoA, respectively=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 $\mu$M and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

Useful inhibitors can also be identified, and potential inhibitors assessed, by in vitro treatment of bacteria and fungi in, for example, culture tubes or Petri dish samples. Such assessments can be performed, for example, by the spreading a measured a liquot of a diluted bacteria culture unto nutrient agar plates, both treated and control, and counting the number of visible cells. Detailed procedures are well known to those skilled in the art as shown for example in Miller, *Experiments in Molecular Genetics*, Cold Spring Harbor Laboratory, 1992.

For example, the effect of the test compound on the virulence of *H. influenzae* is assessed by comparing the survival rates of animals which have been administered the test compound with the survival rate of animals which have not been administered the test compound, wherein a higher survival rate of animal administered the test compound is an indication that the test compound has an effect on the virulence of *H. influenzae.*

To determine the effect of a test compound on colonization of the mucosal surface or on invasiveness and/or virulence of *H. influenzae*, the test compound is administered to the animals either prior to, at the time of, or after inoculation of the animals with *H. influenzae.* The test compound may be administered directly into the nasopharynx, or may be administered by any other route including any one of the traditional modes (e.g. orally, parentally, transdermally or transmuscosally), in a sustained, gels and liposomes, or rectally (e.g. by suppository or enema). Precise formulations and dosages will depend on the nature of the test compound and may be determined using standard techniques, by a pharmacologist of ordinary skill in the art.

Compounds which inhibit either or both phosphopantetheine adenylyltransferase (PPAT, EC 2.7.7.3) and dephospho-CoA kinase (dPCoAK, EC 2.7.1.24) can also be assessed in an animal model, an in vivo test. Such tests can be conducted in an animal which is susceptible to infection by the pathogenic microorganism of interest. In vivo animal model assessments can be conducted, for example, as in U.S. Pat. No. 5,871,951.

3. Useful Inhibitor(s)

The present invention further provides a method for treating pathogenic microorganism infections in a patient by administering to the patient an effective amount of an inhibitor against either or both phosphopantetheine adenylyltransferase (PPAT, EC 2.7.7.3) and dephospho-CoA kinase (dPCoAK, EC 2.7.1.24), wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method. One such inhibitor of phosphopantetheine adenylyltransferase (PPAT, EC 2.7.7.3) is an analogue of a class I aminoacyl-tRNA synthetase since each PPAT subunit displays a dinucleotide binding fold that is structurally similar.

Aminoacyl-tRNA synthetases from all organisms belong to one of two classes depending on the amino acid they are responsible for. Class I enzymes are generally (though not always) monomeric, and attach the carboxyl of their target amino acid to the 2' OH of adenosine 76 in the tRNA molecule. Aminoacyl-tRNA synthetases catalyse a two-step reaction. In the first step they activate their amino acid by forming an aminoacyl-adenylate, in which the carboxyl of the amino acid is linked in to the alpha-phosphate of ATP, by displacing pyrophosphate.

Another such inhibitor of phosphopantetheine adenylyltransferase (PPAT, EC 2.7.7.3) is 3'-dephospho-CoA. Yet another such inhibitor of phosphopantetheine adenylyltransferase (PPAT, EC 2.7.7.3) is deoxycholate.

One such inhibitor of dephospho-CoA kinase (dPCoAK, EC 2.7.1.24) is a compound replacing the 3'-hydroxyl of the ribose such as adenosine diphosphate ribose, on the dephospho-CoA molecule. dPCoAK will not be able to phosphorylate at this site and as a result, CoA will not be produced.

Yet another such inhibitor of dephospho-CoA kinase (dPCoAK, EC 2.7.1.24) is deoxycholate.

Exemplary inhibitors of PPAT, EC 2.7.7.3, are the following:

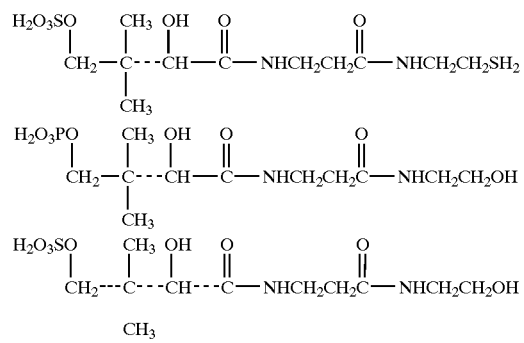

Exemplary inhibitors of dPCoAk, EC 2.7.1.24, are the following:

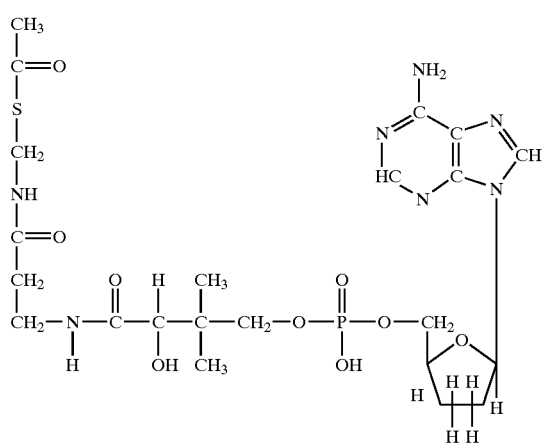

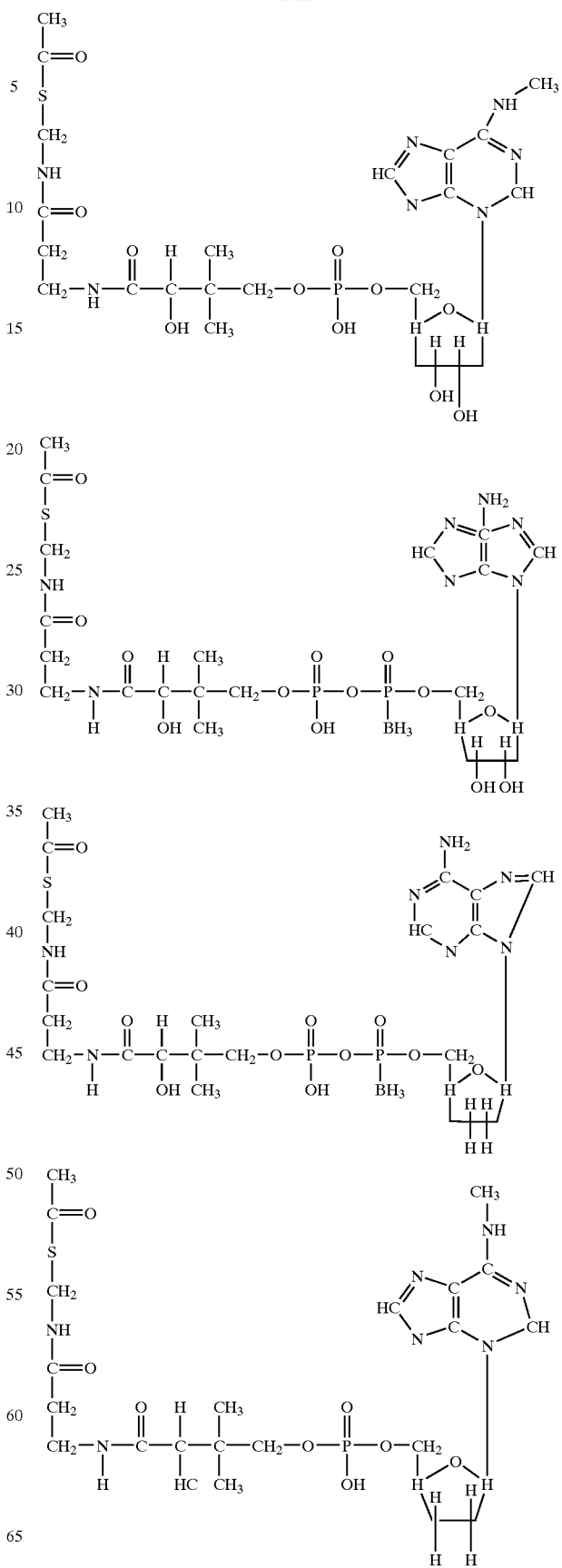

-continued

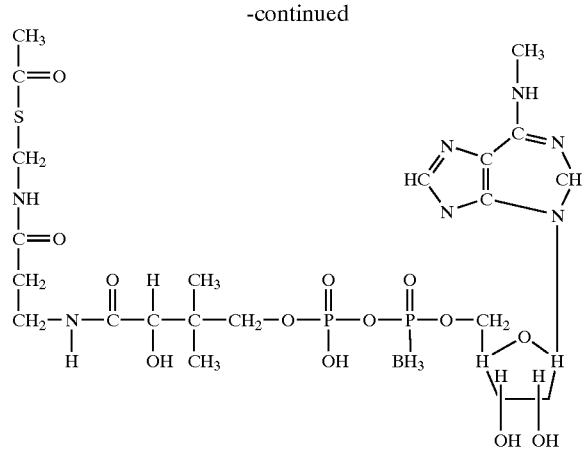

EXAMPLE 3

Biotin

1. Description of the Relevant Pathway(s)

Biotin, a water soluble vitamin biosynthesized by plants and some bacteria and fungi is an essential protein and covalently bound cofactor used in carboxylation reactions central to human metabolism, including enzymes involved in fatty acid biosynthesis, gluconeogenesis, and branched-chain amino acid catabolism. Biotin synthase catalyzes the terminal step in biotin biosynthesis via the insertion of a sulfur atom between C6 and C9 of the precursor dethiobiotin, forming the biotin thioether ring. This insertion reaction is deceptively simple yet represents an impressive feat of enzymatic catalysis, requiring the enzyme break two saturated, unactivated CH bonds in dethiobiotin prior to sulfur insertion. This reaction is catalyzed by the *E. coli* BioB protein, a dimeric iron-sulfur protein, and requires the participation of AdoMet and reduced flavodoxin, indicating that biotin synthase is a member of a family of enzymes that reductively cleave AdoMet to generate a 5,-deoxyadenosyl radical, which is then used to generate a protein radical or to directly abstract a hydrogen atom from the substrate.

The following reactions comprise the metabolism of biotin:

(1) ATP+6-carboxyhexanoate(pimelate)+CoA→AMP+ diphosphate+6-carboxyhexanoyl-CoA(pimeloyl-CoA)

(2) 6-carboxyhexanoyl-CoA+L-alanine→8-amino-7-oxononanoate+CoA+$CO_2$ (3) S-adenosyl-L-methionine+8-amino-7-oxononanoate→S-adenosyl-4-methylthio-2-oxobutanoate+7,8-diaminononanoate (4) ATP+7,8-diaminononanoate+$CO_2$→ADP+ phosphate+dethiobiotin (5) dethiobiotin+sulfur→biotin The present inventor has determined that, since the metabolism of biotin is critical to viability of bacteria and fungi, the inhibition of such pathways in bacteria and fungi provide a novel class of antibiotics for the treatment of bacterial and fungal infections whereas current antibiotics are characterized by inhibition of protein synthesis, DNA synthesis and cell wall synthesis, this novel class of antibiotics is characterized by inhibition of biotin metabolism.

The inventor has particularly noted that production of biotin is critical to viability of bacteria and fungi and since four of the five enzymes in the pathway, 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6) are not present in mammals, the enzymes provide excellent targets for inhibition of bacterial and fungal growth, thereby providing a means for inhibiting the growth of microorganisms and treating bacterial and fungal infections.

The present inventor has discovered that while certain important pathogenic microorganisms require the activity of 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6) to produce biotin, that enzyme is not present in mammals, particularly not in humans. As a result, the present inventor has first determined that inhibition of any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6) provides an excellent target for inhibiting the growth of pathogenic microorganisms, while not inhibiting any important biosynthetic pathway in humans.

The metabolic pathway leading to the production of biotin is as follows:

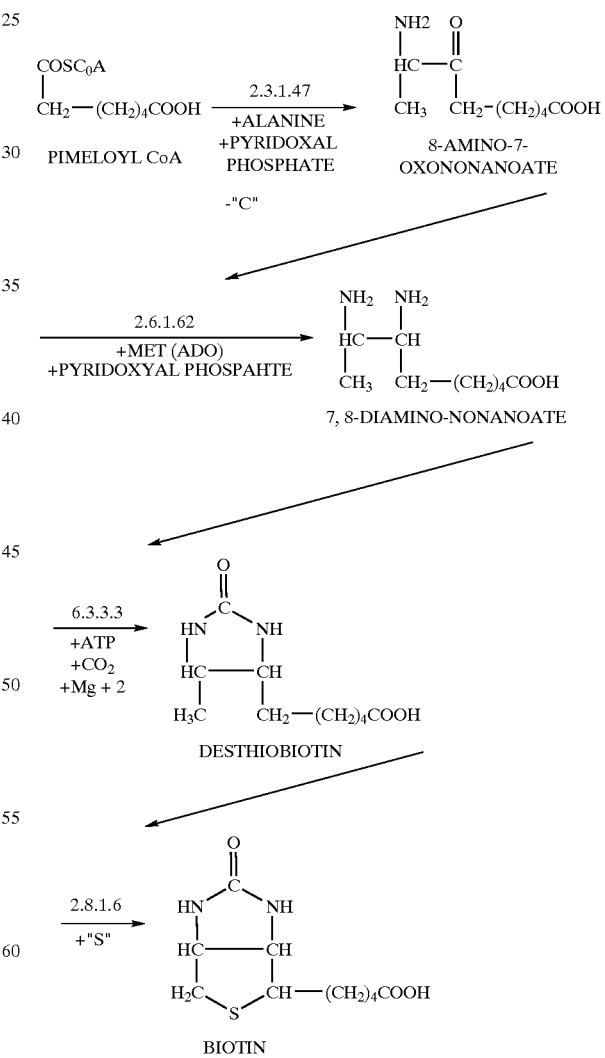

As noted above, in bacteria and fungi, 8-amino-7-oxononanoate synthase (EC2.3.1.47) catalyzes the reaction of Pimeloyl-CoA to produce 8-Amino-7-oxononanoate; adenosylmethionine-8-amino-7-oxononanoate transaminase (EC2.6.1.62) catalyzes the reaction of 8-Amino-7-oxononanoate to produce 7,8-Diamino-nonanoate; dethiobiotin synthase (EC6.3.3.3) catalyzes the reaction of 7,8-Diamino-nonanoate to produce dethiobiotin; and biotin synthase (EC 2.8.1.6) catalyzes the reaction of dethiobiotin to produce biotin.

As is well known, antibiotics are currently used to treat a wide range of bacterial and fungal infections, ranging from minor to life threatening infections. Broad spectrum antibiotics treat a variety of gram-positive and gram-negative bacteria and fungal organisms, while mild spectrum antibiotics only cover limited types of bacterial and fugal organisms and are useful for curing infections with known bacterial and fungal strains.

But it has recently been noted that pathogenic bacteria and fungi increasingly exhibit resistance to existing classes of antibiotics, such as penicillin, vancomycin and erythromycin. According to the Center for Disease Control, pathogenic resistance has significantly increased mortality rates, making infectious disease the third largest cause of death in the United States. The rates of antibiotic resistant bacteria have particularly increased recently with respect to *S. aureus, Enterococcus* strains, *S. pneumoniae* and *tuberculosis*.

The mechanism of action for most antibiotics is the inhibition of bacterial cell wall completion, or DNA or protein synthesis. Sulfonamides and trimethoprin act by inhibiting an essential metabolic step, namely folate synthesis. But there is a great need for new antibiotics with different targets, especially in light of the ever increasing problem of resistant strains.

The present inventor has found that compounds which act as inhibitors of any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6) offer another class of antibiotics which inhibit an essential metabolic step, namely a pathway essential for bacterial and fungal biotin metabolism.

According to the present invention, an enzyme in a biotin pathway which is important for continued growth and viability of a pathogenic microorganism but which is absent in humans provides a unique, specific target for compounds which can inhibit infections of such pathogenic microorganisms without causing undesirable side effects or toxicity to a mammalian patient. Various biosynthetic pathways have been identified in the literature for various microorganisms and for mammals, and those pathways, which include an important enzyme present in pathogenic microorganisms but absent in mammals, provide a unique target for screening for compounds useful for inhibiting pathogenic microorganism infections.

According to the present invention, the present inventor has specifically identified any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6) as an enzyme present in an important biosynthetic pathway for pathogenic microorganisms, but absent in mammals, specifically absent in humans. Since the biosynthetic pathway is important for biotin metabolism in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic bacterial and fungal microorganisms which require any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6), including *Yersinia pestis, Pseudomonas aeruginosa, Neisseria meningitides* serogroup A and B, *Helicobacter pylori, Chlamydia pneumoniae, Haemophilus influenzae, Mycobacterium leprae, Mycobacterium tuberculosis, Vibrio cholerae, Staphylococcus aureus*.

2. Description of Method for Inhibition Screening

As noted above, one aspect of the present invention is a method for the identification of a compound capable of inhibiting the growth of pathogenic microorganisms by interfering with the activity of any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6). Compounds can be identified by incubating a sample of bacteria in a solution containing a known amount of 8-Amino-7-oxononanoate; 7,8-Diamino-nonanoate; or dethiobiotin in the presence or absence of a test compound, assessing the effect on conversion of any of the enzymes in the pathway, namely 8-amino-7-oxononanoate synthase (EC2.3.1.47); adenosyhnethionine-8-amino-7-oxononanoate transaminase (EC2.6.1.62); dethiobiotin synthase (EC6.3.3.3); and biotin synthase (EC 2.8.1.6) wherein, a lower level of conversion in the presence of the test compound, compared with the level of conversion in the absence of the test compound, indicates that the test compound inhibits the activity of the enzyme.

Compounds capable of inhibiting any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6) can also be identified by means of in vitro experiments by exposing a substrate comprising 8-Amino-7-oxononanoate; 7,8-Diamino-nonanoate; or dethiobiotin to a plurality of test compounds and identifying those compounds which inhibit the tested enzyme according to known catalytic measurement techniques.

One particular in vitro method for assessing the activity of an inhibitor to any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6):

Enzyme assays are performed at a subsaturating concentration of substrate (depending on the enzyme, 0.2–1 mM, 8-Amino-7-oxononanoate; 7,8-Diamino-nonanoate; or dethiobiotin=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 $\mu$M and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

3. Useful Inhibitor(s)

Useful inhibitors can also be identified, and potential inhibitors assessed, by in vitro treatment of bacteria and fungi in, for example, culture tubes or petri dish samples. Such assessments can be performed, for example, by spreading a measure aliquot of a diluted bacteria culture onto nutrient agar plates, both treated and control, and counting the number of visible cells. Detailed procedures are will known to those skilled in the art, as shown for example in Miller, *Experiments in Molecular Genetics*, Cold Spring Harbor Laboratory, 1992.

Compounds which inhibit any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC2.8.1.6) can also be assessed in an animal model, an in vivo test. Such tests can be conducted in an animal which is susceptible to infection by the pathogenic microorganism of interest. In vivo animal model assessments can be conducted.

For example, the effect of the test compound on the virulence of *H. influenzae* is assessed by comparing the survival rates of animals which have been administered the test compound with the survival rate of animals which have not been administered the test compound, wherein a higher survival rate of animals administered the test compound is an indication that the test compound has an effect on the virulence of *H. influenzae*.

To determine the effect of a test compound on colonization of the mucosal surface or on invasiveness and/or virulence of *H. influenzae*, the test compound is administered to the animals either prior to, at the time of, or after inoculation of the animals with *H. influenzae*. The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

The present invention further provides a method for treating pathogenic microorganism infections in a patient by administering to the patient an effective amount of an inhibitor against any of the enzymes in the pathway, namely 8-amino-7-oxononanoate synthase (EC2.3.1.47); adenosylmethionine-8-amino-7-oxononanoate transaminase (EC2.6.1.62); dethiobiotin synthase (EC6.3.3.3); and biotin synthase (EC 2.8.1.6), wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method. Exemplary inhibitors of 8-amino-7-oxononanoate synthase (EC2.3.1.47) have the following structures:

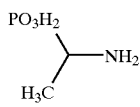
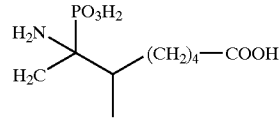

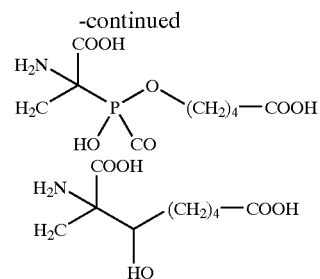

Exemplory Inhibitors of adenosylmethionine-8-amino-7-oxononanoate transaminase (EC 2.6.1.6.2) have the following structure:

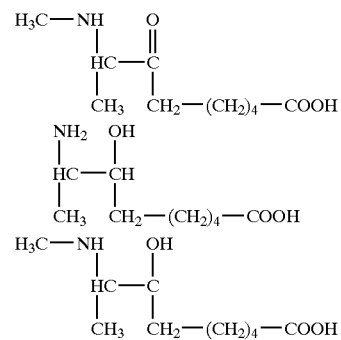

Exemplory inhibitors of dethiobiotin synthase (EC6.3.3.3) has the following structure:

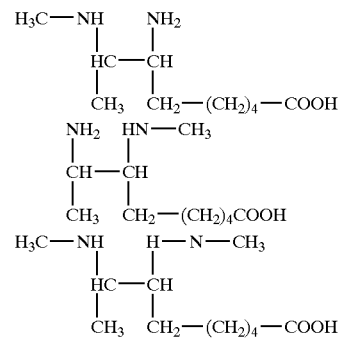

Exemplory inhibitors of biotin synthase (EC 2.8.1.6) have the folooowing structure:

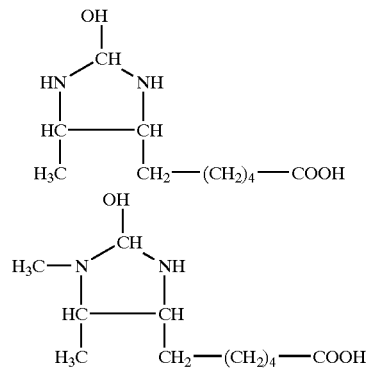

-continued

[Chemical structures with formulas including H3C-N, NH, HC-CH, H3C, CH2-(CH2)4-COOH groups; and similar variants with OH, =O substituents]

The above compounds, can be prepared by those skilled in the art by known procedures for derivatizing the substrate compounds in the biotin synthesis pathway.

EXAMPLE 4

PEP Carboxylase

1. Description of the Relevant Pathway(s)

Plants and photosynthetic bacteria have adapted different ways of initially fixing $CO_2$ prior to its entering the Calvin cycle. The pathway of carbon fixation used by photosynthetic bacteria is known as the $C_4$ pathway.

The $C_4$ pathway is designed to efficiently fix $CO_2$ at low concentrations. Photosynthetic bacteria fix $CO_2$ from a three-carbon compound called phosphoenolpyruvate to produce the four-carbon compound oxaloacetate (OAA) The enzyme catalyzing this reaction, Phosphoenolpyruvate (PEP) carboxylase (EC4.1.1.31). OAA is an intermediate in several important pathways, including gluconeogenesis, the Krebs Cycle (citric acid cycle), glyoxylate cycle, urea cycle, and amino acid metabolism The following reaction comprises the reductive carboxylate cycle in photosynthetic bacteria:

(6) Phosphoenolpyruvate + $CO_2$ + $H_2O$ ⟶ Oxaloacetate + phosphate

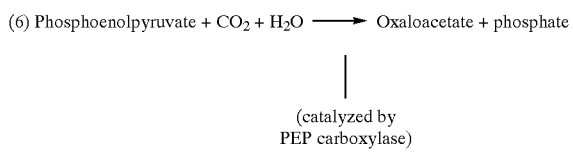

(catalyzed by PEP carboxylase)

[Reaction scheme: PHOSPHOENOLPYRUVATE (COOH-C(O-P(OH)2=O)=CH2) → via PEP carboxylase (4.1.1.31) +$CO_2$+$H_2O$ releasing $P_i$, or via PEP Carboxykinase (4.1.1.38) +$CO_2$+$P_i$ releasing $PP_i$ → OXALOACETATE (COOH-CH2-C(=O)-COOH)]

The present inventor has determined that, since the reductive carboxylate cycle in photosynthetic bacteria is critical to viability of these bacteria, the inhibition of such pathways in bacteria provides a novel class of antibiotics for the treatment of bacterial infections. Whereas current antibiotics are characterized by inhibition of protein synthesis, DNA synthesis and cell wall synthesis, this novel class of antibiotics is characterized by inhibition of the reductive carboxylate cycle in photosynthetic bacteria.

The inventor has particularly noted that production of oxoloacetate (OAA), is critical to viability of bacteria and since (PEP) carboxylase (EC4.1.1.31) is not present in mammals, the enzyme provides an excellent target for inhibition of bacterial growth, thereby providing a means for inhibiting the growth of microorganisms and treating bacterial infections.

The present inventor has discovered that while certain important pathogenic microorganisms require the activity (PEP) carboxylase (EC4.1.1.31) to produce oxoloacetate, that enzyme is not present in mammals, particularly not in humans. As a result, the present inventor has first determined that inhibition of (PEP) carboxylase (EC4.1.1.31) provides an excellent target for inhibiting the growth of pathogenic microorganisms, while not inhibiting any important biosynthetic pathway in humans.

As noted above, in photosynthetic bacteria, (PEP) carboxylase (EC4.1.1.31) catalyzes the reaction of phosphoenol pyruvate, carbon dioxide, and water to produce oxoloacetate. The present inventor has found that compounds which act as inhibitors of (PEP) carboxylase (EC4.1.1.31) offer another class of antibiotics which inhibit an essential metabolic step, namely a pathway essential for photosynthetic bacterial reductive carboxylation.

According to the present invention, an enzyme in the reductive carboxylate pathway which is important for continued growth and viability of a pathogenic microorganism but which is absent in humans provides a unique, specific target for compounds which can inhibit infections of such pathogenic microorganisms without causing undesirable side effects or toxicity to a mammalian patient. Various biosynthetic pathways have been identified in the literature for various microorganisms and for mammals, and those pathways, which include an important enzyme present in pathogenic microorganisms but absent in mammals, provide a unique target for screening for compounds useful for inhibiting pathogenic microorganism infections.

According to the present invention, the present inventor has specifically identified (PEP) carboxylase (EC4.1.1.31) as an enzyme present in an important biosynthetic pathway for pathogenic microorganisms, but absent in mammals, specifically absent in humans. Since the biosynthetic pathway is important for reductive carboxylation in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic bacterial microorganisms which require (PEP) carboxylase (EC4.1.1.31), including *Pseudomonas aeruginosa, Streptococcus pyogenes, Yersinia pestis, Neisseria meningitides* serogroupA and B, *Esherichia coli* O157*, Haemophilus influenzae, Mycobacterium leprae, Vibrio cholerae,* and *Streptococcus pneumoniae.*

2. Description of Method for Inhibition Screening

As noted above, one aspect of the present invention is a method for the identification of a compound capable of inhibiting the growth of pathogenic microorganisms by interfering with the activity of (PEP) carboxylase (EC4.1.1.31). Compounds can be identified by incubating a sample of bacteria in a solution containing a known amount of phosphoenol pyruvate in the presence or absence of a test compound, assessing the effect on conversion of phosphoenol pyruvate; wherein, a lower level of conversion in the presence of the test compound, compared with the level of conversion in the absence of the test compound, indicates that the test compound inhibits the activity of the enzyme.

Compounds capable of inhibiting (PEP) carboxylase (EC4.1.1.31) can also be identified by means of in vitro experiments by exposing a substrate comprising phosphoenol pyruvate to a plurality of test compounds and identifying those compounds which inhibit the tested enzyme according to known catalytic measurement techniques.

One particular in vitro method for assessing the activity of an inhibitor to (PEP) carboxylase (EC4.1.1.31):

Enzyme assays are performed at a subsaturating concentration of substrate (depending on the enzyme, 0.2–1 mM,phosphoenol pyruvate=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 μM and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

Useful inhibitors can also be identified, and potential inhibitors assessed, by in vitro treatment of bacteria in, for example, culture tubes or petri dish samples. Such assessments can be performed, for example, by spreading a measured aliquot of a diluted bacterial culture into nutrient agar plates, both treated and control, and counting the number of visible cells. Detailed procedures are well known to those in the art, as shown for example in Miller, *Experiments in Molecular Genetics*, Cold Spring Harbor Laboratory, 1972.

Compounds which inhibit (PEP) carboxylase (EC4.1.1.31) can also be assessed in an in vivo animal model test, such as for example as described in U.S. Pat. No. 5,871,951. Such tests can be conducted in an animal which is susceptible to infection by the pathogenic microorganism of interest. For example, the effect of the test compound on the virulence of *H. influenzae* is assessed by comparing the survival rates of animals which have been administered the test compound with the survival rate of animals which have not been administered the test compound, wherein a higher survival rate of animals administered the test compound is an indication that the test compound has an effect on the virulence of *H. influenzae.*

To determine the effect of a test compound on colonization of the mucosal surface or on invasiveness and/or virulence of *H. influenzae*, the test compound is administered to the animals either prior to, at the time of, or after inoculation of the animals with *H. influenzae*. The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

The present invention further provides a method for treating pathogenic microorganism infections in a patient by administering to the patient an effective amount of an inhibitor against (PEP) carboxylase (EC4.1.1.31), wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method.

3. Useful Inhibitor(s)

Useful inhibitors are structural analogues of phosphoenolpyruvate which bind to PEP carboxylase but are not converted to oxaloacetate. Such structural analogues compete with the PEP substrate, thus inhibiting the production of oxaloacetate. Exemplary useful inhibitors, which can be prepared according to procedures well known to those skilled in the art, are the following:

Inhibitors/Structural Analogues of PEP

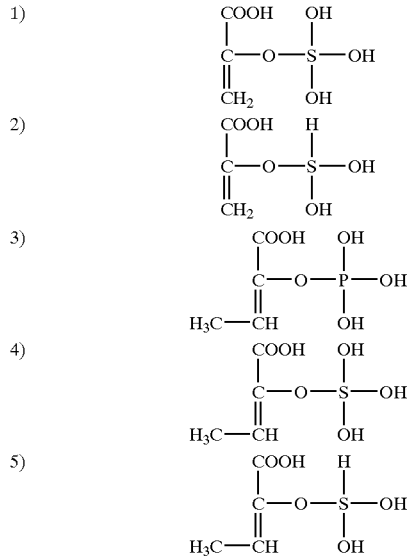

EXAMPLE 5

Riboflavin

1. Description of the Relevant Pathway(s)

Riboflavin, vitamin $B_2$, is the precursor of flavin mononucleotide and flavin adenine dinucleotide, essential cofactors for a multitude of mainstream metabolic enzymes that mediate hydride, oxygen, and electron transfer reactions. Consequently, critical cellular processes as diverse as the citric acid cycle, fatty acid oxidation, photosynthesis, mitochondrial electron transport, and de novo pyrimidine biosynthesis are fundamentally dependent on riboflavin availability. Despite its essentiality, however, only plants and certain microorganisms can synthesize vitamin $B_2$, whereas higher animals, including man, must obtain it through their diet.

In contrast, flavokinase and FAD pyrophosphorylase, the enzymes that convert riboflavin to flavin mononucleotide (FMN) and flavin adenine dinucleotide (FAD), respectively, are widely distributed in nature. Our current knowledge of riboflavinbiosynthesis is largely restricted to bacteria and yeast. In both cases, the synthetic pathway consists of seven distinct enzyme-catalyzed reactions, with GTP and ribulose 5-phosphate the ultimate, noncommitted precursors. Although the sequence of events that are catalyzed in the second and third steps occur in opposite order in bacteria and fungi, the remaining pathway intermediates are identical in both types of microorganisms.

The last two enzymes of riboflavin biosynthesis, lumazine synthase (LS) and riboflavin synthase (RS) (EC2.5.1.9), are the best characterized, both structurally and mechanistically. LS catalyzes the penultimate step of riboflavin biosynthesis, namely the condensation of 3,4-dihydroxy-2-butanone 4-phosphate (DHBP) with 5-amino-6-ribitylamino-2,4(1H,3H)-pyrimidinedione (ARAPD) to yield one molecule each of orthophosphate and 6,7-dimethyl-8-ribityllumazine (DMRL). The latter is the immediate precursor of riboflavin.

The ultimate step of riboflavin biosynthesis is mediated by RS, which catalyzes the dismutation of two molecules of DMRL to yield one molecule of riboflavin and one molecule of ARAPD.

The following reactions comprise the biosynthesis of riboflavin (with the catalyzing enzyme following in parenthesis):

(7) GTP+3H$_2$O→formate+2,5-diamino-6-hydroxy-4-(5-phosphoribosylamino)-pyrimidine+diphosphate (GTP cyclohydrolase II; EC 3.5.4.25)

(8) 2,5-diamino-6-hydroxy-4-(5-phosphoribosylamino)-pyrimidine+H$_2$O→5-amino-6-(5-phosphoribosylamino)uracil+NH$_3$ (diaminohydroxyphosphoribosylaminopyrimidine deaminase; EC 3.5.4.26)

(9) 5-amino-6-(5-phosphoribitylamino)uracil+NADP→5-amino-6-(5-phosphoribosylamino)uracil+NADPH$_2$(5-amino-6-(5-phosphoribosylamino)uracil reductase; EC 1.1.1.193)

(10) 3,4-dihydroxy-2-butanone 4-phosphate (DHBP)+5-amino-6-ribitylamino-2,4(1H,3H)-pyrimidinedione (ARAPD)→orthophosphate and 6,7-dimethyl-8-ribityllumazine (DMRL) (lumazine synthase)

(11) orthophosphate and 6,7-dimethyl-8-ribityllumazine (DMRL)+riboflavin+4-(1-D-ribitylamino)-5-amino-2,6-dihydroxypyrimidine(riboflavin synthase; EC 2.5.1.9)

Scheme 1 shows schematically the final steps leading to riboflavin. Step A is catalyzed by lumazine synthase and step B is catalyzed by riboflavin synthase. Both enzymes are suitable targets for antimicrobial therapy. Specific inhibitors would not interfere with human metabolism as humans do not posses the corresponding isoenzymes.

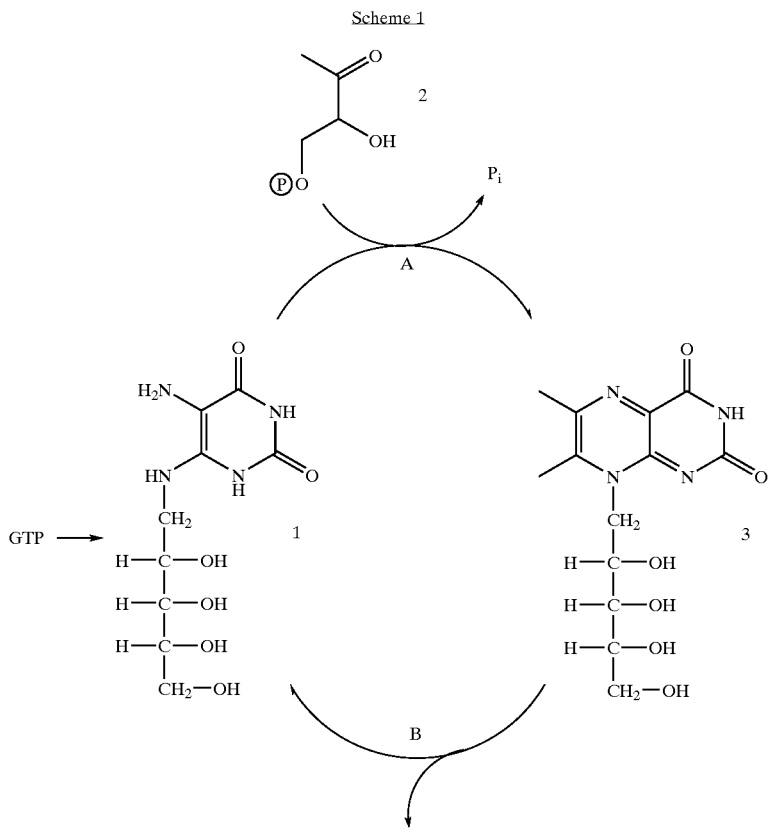

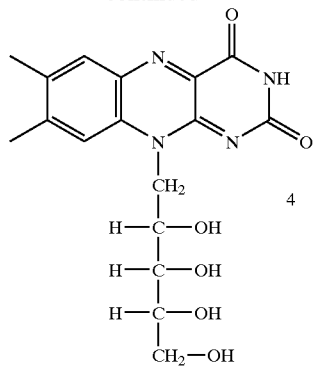

The present inventor has determined that, since the biosynthesis of riboflavin is critical to viability of bacteria and fungi, the inhibition of such pathways in bacteria and fungi provides a novel class of antibiotics for the treatment of bacterial and fungal infections. Whereas current antibiotics are characterized by inhibition of protein synthesis, DNA synthesis and cell wall synthesis, this novel class of antibiotics is characterized by inhibition of riboflavin biosynthesis.

The inventor has particularly noted that production of riboflavin is critical to viability of bacteria and fungi and since all of the enzymes are not present in mammals, those enzymes provide an excellent target for inhibition of bacterial and fungal growth, thereby providing a means for inhibiting the growth of microorganisms and treating bacterial and fungal infections.

The present inventor has discovered that while certain important pathogenic microorganisms require the activity of GTP cyclohydrolase II (EC 3.5.4.25); diaminohydroxyphosphoribosylaminopyrimidine deaminase (EC 3.5.4.26); 5-amino-6-(5-phosphoribosylarnino)uracil reductase (EC 1.1.1.193); lumazine synthase; and riboflavin synthase (EC 2.5.1.9) to produce riboflavin, that enzyme is not present in mammals, particularly not in humans. As a result, the present inventor has first determined that inhibition of any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino)uracil reductase (EC 1.1.1.193); lumazine synthase; and riboflavin synthase (EC 2.5.1.9) provides an excellent target for inhibiting the growth of pathogenic microorganisms, while not inhibiting any important biosynthetic pathway in humans.

As noted above, in bacteria and fungi, GTP cyclohydrolase II (EC 3.5.4.25) catalyzes the reaction of GTP with a purine to produce 2,5-Diamino-6-hydroxy-4-(5'phosphoribosylamino)-pyrimidine; diaminohydroxyphosphoribosylaminopyrimidine deaminase (EC 3.5.4.26) catalyzes the reaction of 2,5-Diamino-6-hydroxy-4-(5'phosphoribosylamino)-pyrimidine to produce 5-amino-6-(5-phosphoribosylamino)uracil; 5-amino-6-(5-phosphoribosylamino)uracil reductase (EC 1.1.1.193) catalyzes the reaction of 5-amino-6-(5-phosphoribosylamino)uracil to produce 5-Amino-6-(5'phosphoribitylamino)uracil; lumazine synthase catalyzes the reaction of 5-Amino-6-(5'phosphoribitylamino)uracil to produce 6,7-Dimethyl-8-ribityl lumazine; and riboflavin synthase (EC 2.5.1.9) catalyzes the reaction of 6,7-Dimethyl-8-ribityl lumazine to produce riboflavin The present inventor has first recognized the importance of this distinction in providing a target for inhibition of pathogenic microorganisms.

As is well known, antibiotics are currently used to treat a wide range of bacterial and fungal infections, ranging from minor to life threatening infections. Broad spectrum antibiotics treat a variety of gram-positive and gram-negative bacteria and fungal organisms, while mild spectrum antibiotics only cover limited types of bacterial and fungal organisms and are useful for curing infections with known bacterial and fungal strains.

The present inventor has found that compounds which act as inhibitors of any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino)uracil reductase (EC 1.1.1.193); lumazine synthase; and riboflavin synthase (EC 2.5.1.9) offer another class of antibiotics which inhibit an essential metabolic step, namely a pathway essential for bacterial and fungal riboflavin biosynthesis.

According to the present invention, an enzyme in a riboflavin pathway which is important for continued growth and viability of a pathogenic microorganism but which is absent in humans provides a unique, specific target for compounds which can inhibit infections of such pathogenic microorganisms without causing undesirable side effects or toxicity to a mammalian patient. Various biosynthetic pathways have been identified in the literature for various microorganisms and for mammals, and those pathways, which include an important enzyme present in pathogenic microorganisms but absent in mammals, provide a unique target for screening for compounds useful for inhibiting pathogenic microorganism infections.

According to the present invention, the present inventor has specifically identified any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino) uracil reductase (EC 1.1.1.193); lumazine synthase; and riboflavin synthase (EC 2.5.1.9) as an enzyme present in an important biosynthetic pathway for pathogenic microorganisms, but absent in mammals, specifically absent in humans. Since the biosynthetic pathway is important for riboflavin biosynthesis in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic bacterial and fungal microorganisms which require any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino)uracil reductase (EC 1.1.1.193); lumazine synthase; and riboflavin synthase (EC 2.5.1.9), including *Yersinia pestis, Pseudomonas aeruginosa, Neisseria meningitides* serogroup A and B, *Helicobacter pylori, Chlamydia trachomatis, Chlamydia pneumoniae, Streptococcus pneumoniae, Haemophilus influenzae, Mycobacterium leprae, Mycobacterium tuberculosis, Vibrio cholerae, Staphylococcus aureus.*

2. Description of Method for Inhibition Screening

As noted above, one aspect of the present invention is a method for the identification of a compound capable of inhibiting the growth of pathogenic microorganisms by interfering with the activity of any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino) uracil reductase (EC 1.1.1.193); lumazine synthase; and riboflavin synthase (EC 2.5.1.9). Compounds can be identified by incubating a sample of bacteria in a solution containing a known amount of 2,5-Diamino-6-hydroxy-4-(5'phosphoribosylamino)-pyrimidine; 5-amino-6-(5-phosphoribosylamino)uracil; 5-Amino-6-(5'phosphoribitylamino)uracil; or 6,7-Dimethyl-8-ribityl lumazine; in the presence or absence of a test compound, assessing the effect on conversion of any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino) uracil reductase (EC 1.1.1.193); lumazine synthase; and riboflavin synthase (EC 2.5.1.9) wherein, a lower level of conversion in the presence of the test compound, compared with the level of conversion in the absence of the test compound, indicates that the test compound inhibits the activity of the enzyme.

Compounds capable of inhibiting any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino) uracil reductase (EC 1.1.1.193); lumazine synthase; and riboflavin synthase (EC 2.5.1.9) can also be identified by means of in vitro experiments by exposing a substrate comprising 2,5-Diamino-6-hydroxy-4-(5'phosphoribosylamino)-pyrimidine; 5-amino-6-(5-phosphoribosylamino)uracil; 5-Amino-6-(5'phosphoribitylarnino)uracil; or 6,7-Dimethyl-8-ribityl lumazine to a plurality of test compounds and identifying those compounds which inhibit the tested enzyme according to known catalytic measurement techniques.

One particular in vitro method for assessing the activity of an inhibitor to any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino)uracil reductase (EC 1.1.1.193); lumazine synthase; and riboflavin synthase (EC 2.5.1.9):

Enzyme assays are performed at a subsaturating concentration of substrate (depending on the enzyme, 0.2–1 mM, 2,5-Diamino-6-hydroxy-4-(5'phosphoribosylamino)-pyrimidine; 5-amino-6-(5-phosphoribosylamino)uracil; 5-Amino-6-(5'phosphoribitylamino)uracil; or 6,7-Dimethyl-8-ribityl lumazine=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 μM and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

Useful inhibitors can also be identified, and potential inhibitors assessed, by in vitro treatment of bacteria in, for example, culture tubes or petri dish samples. Such assessments can be performed, for example, by spreading a measured aliquot of a diluted bacterial culture into nutrient agar plates, both treated and control, and counting the number of visible cells. Detailed procedures are well known to those in the art, as shown for example in Miller, *Experiments in Molecular Genetics*, Cold Spring Harbor Laboratory, 1972.

Compounds which inhibit any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino) uracil reductase (EC 1.1.1.193); lumazine synthase; and riboflavin synthase (EC 2.5.1.9) can also be assessed in an animal model, an in vivo test. Such tests can be conducted in an animal which is susceptible to infection by the pathogenic microorganism of interest. In vivo animal model assessments can be conducted, for example, as described in U.S. Pat. No. 5,871,951.

For example, the effect of the test compound on the virulence of *H. influenzae* is assessed by comparing the survival rates of animals which have been administered the test compound with the survival rate of animals which have not been administered the test compound, wherein a higher survival rate of animals administered the test compound is an indication that the test compound has an effect on the virulence of *H. influenzae.*

To determine the effect of a test compound on colonization of the mucosal surface or on invasiveness and/or virulence of *H. influenzae*, the test compound is administered to the animals either prior to, at the time of, or after inoculation of the animals with *H. influenzae*. The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

3. Useful Inhibitors

The present invention further provides a method for treating pathogenic microorganism infections in a patient by administering to the patient an effective amount of an inhibitor against any of the enzymes in the pathway, namely GTP cyclohydrolase II (EC 3.5.4.25); diaminohydroxyphosphoribosylaminopyrimidine deaminase (EC 3.5.4.26); 5-amino-6-(5-phosphoribosylamino)uracil reductase (EC 1.1.1.193); lumazine synthase; and riboflavin synthase (EC 2.5.1.9),wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method. Useful inhibitors of lumazine synthase and riboflavin synthase (EC 2.5.1.9) have the following structures:

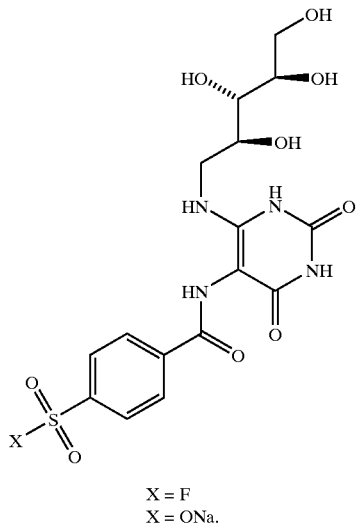

X = F
X = ONa.

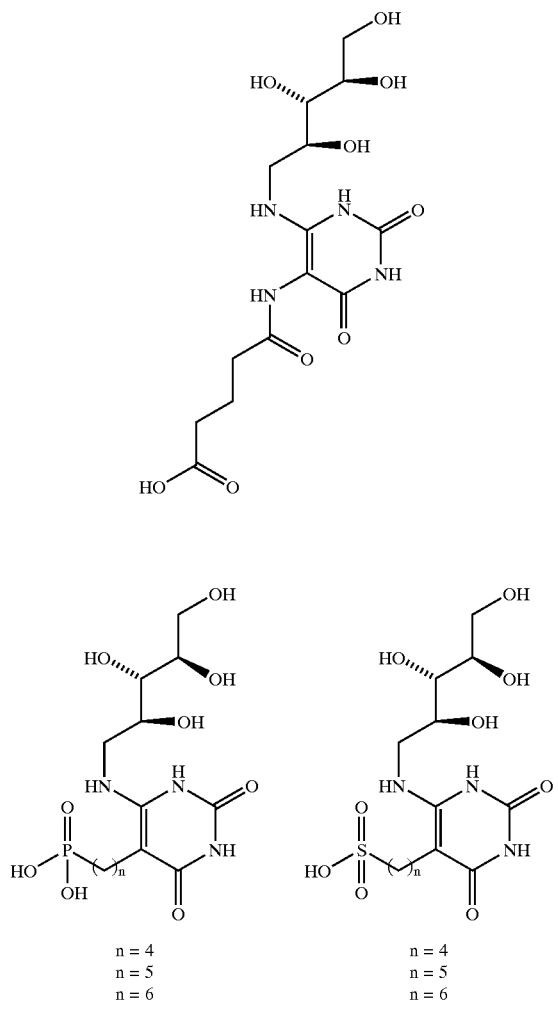

n = 4
n = 5
n = 6 n = 4
n = 5
n = 6

-continued

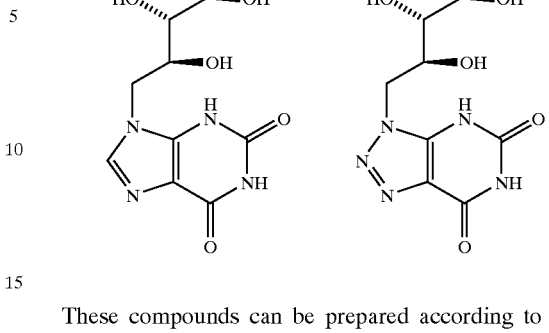

These compounds can be prepared according to procedures described in Cushman, M. et al, *Design, Synthesis and Biological Evaluation of Homologous Phosphonic Acids and Sulfonic Acids as Inhibitors of Lumazine Synthase*, J. Org. Chem. 1999, 64, 3838–3845 and Cushman, M. et al, *Design and Synthesis of 6-(6-D-Ribitylamino-2-4-dihdroxypyrimidin-5-yl)-1-hexylphosphonic acid, a Potent Inhibitor of Lumazine Synthase*, Bioorganic & Medicinal Chemistry Letters 9 (1999) 39–42.

EXAMPLE 6

Thiamine

1. Description of the Relevant Pathway(s)

Thiamine is a water-soluble B-complex vitamin, previously known as vitamin B-1 or aneurine. Isolated and characterized in the 1930's, thiamin was one of the first organic compounds to be recognized as a vitamin. Thiamin occurs in the human body as free thiamine and its phosphorylated forms: thiamine monophosphate (TMP), thiamine triphosphate (TTP), and thiamine pyrophosphate (TPP), which is also known as thiamine diphosphate.

The chemical name for this water souble vitamin is 3-[(4-amino-2-methyl-5-pyrimidinyl)methyl]-5-(2-hydroxyethyl)-4-methylthiazolium. Thiamine consist of a pyrimidine ring and a thiazole ring connected by a one carbon link. The nitrogen in the thiazole ring has a charge of +1. This nitrogen atom serves as an important electron sink in thiamine pyrophosphate mediated reactions.

A major biologically active form of thiamine is thiamine pyrophosphate (TPP), sometimes called thiamine diphosphate (TDP) and cocarboxylase. TPP is a coenzyme for two types of enzymes, alpha-ketoacid dehydrogenases and transketolases, both of which cleave a C—C bond adjacent to a carbonyl group releasing either carbon dioxide or an aldehyde.

The Krebs cycle (also called the citric acid cycle and the tricarboxylic acid cycle) is very important in extracting energy from fuel molecules. TPP is the coenzyme for alpha-ketoacid dehydrogenases which catalyze two reactions of the Krebs cycle.

The oxidative decarboxylation of pyruvate to acetyl CoA

The oxidative decarboxylation of alpha-ketoglutarate to succinyl CoA

The pentose phosphate pathway harvests energy from fuel molecules and stores it in the form of NADPH. NADPH (reduced nicotinamide adenine dinucleotide phosphate) is an important electron donor in reductive biosynthesis. The pentose phosphate pathway also produces 5-carbon sugars such as ribose which is used in the synthesis of DNA and RNA. TPP is the coenzyme for the enzyme transketolase. Transketolase transfers a 2-carbon unit from an alpha-ketose (a sugar with a carbonyl group at position 2) to an aldose.

The following reactions comprise the biosynthesis of thiamine: Thiamine biosynthesis begins with purine metabolism. From here AIR synthetase, the fifth step in the pathway catalyzes the conversion of 5'-phosphoribosyl-N-formylglycinamidine (FGAM) to 5'-phosphoribosyl-5-aminoimidazole (AIR). 4-Amino-5-hydroxymethyl-2-methylpyrimidine is then formed in a series of reactions.

(12) ATP+4-amino-5-hydroxymethyl-2-methylpyrimidine→ADP+4-amino-5-phosphomethyl-2-methylpyrimidine(hydroxymethylpyrimidine kinase; EC 2.7.1.49)

(13) ATP+4-amino-2-methyl-5-phosphomethylpyrimidine→ADP+4-amino-2-methyl-5-diphosphomethylpyrimidine (phosphomethylpyrimidine kinase; EC 2.7.4.7)

(14) 2-methyl-4-amino-5-hydroxymethylpyrimidine diphosphate+4-methyl-5-(2-phosphono-oxyethyl) thiazole→diphosphate+thiamine monophosphate (thiamine-phosphate diphosphorylase; EC 2.5.1.3)

(15) thiamine monophosphate→thiamine (phosphohistidine phosphatase; EC 3.1.3.-)

The present inventor has determined that, since the biosynthesis of thiamine is critical to viability of bacteria and fungi, the inhibition of such pathways in bacteria and fungi provide a novel class of antibiotics for the treatment of bacterial and fugal infections whereas current antibiotics are characterized by inhibition of protein synthesis, DNA synthesis and cell wall synthesis, this novel class of antibiotics is characterized by inhibition of thiamine biosynthesis.

The inventor has particularly noted that production of thiamine, is critical to viability of bacteria and fungi and since the last three enzymes are not present in mammals, the enzymes provides an excellent target for inhibition of bacterial and fungal growth, thereby providing a means for inhibiting the growth of microorganisms and treating bacterial and fungal infections.

The present inventor has discovered that while certain important pathogenic microorganisms require the activity of phosphomethylpyrimidine kinase; (EC 2.7.4.7), thiamine-phosphate diphosphorylase; (EC 2.5.1.3), and phosphohistidine phosphatase; (EC 3.1.3.-) to produce thiamine, that enzyme is not present in mammals, particularly not in humans. As a result, the present inventor has first determined that inhibition of any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-) provides an excellent target for inhibiting the growth of pathogenic microorganisms, while not inhibiting any important biosynthetic pathway in humans.

The metabolic pathway leading to the production of thiamine comprises the following:

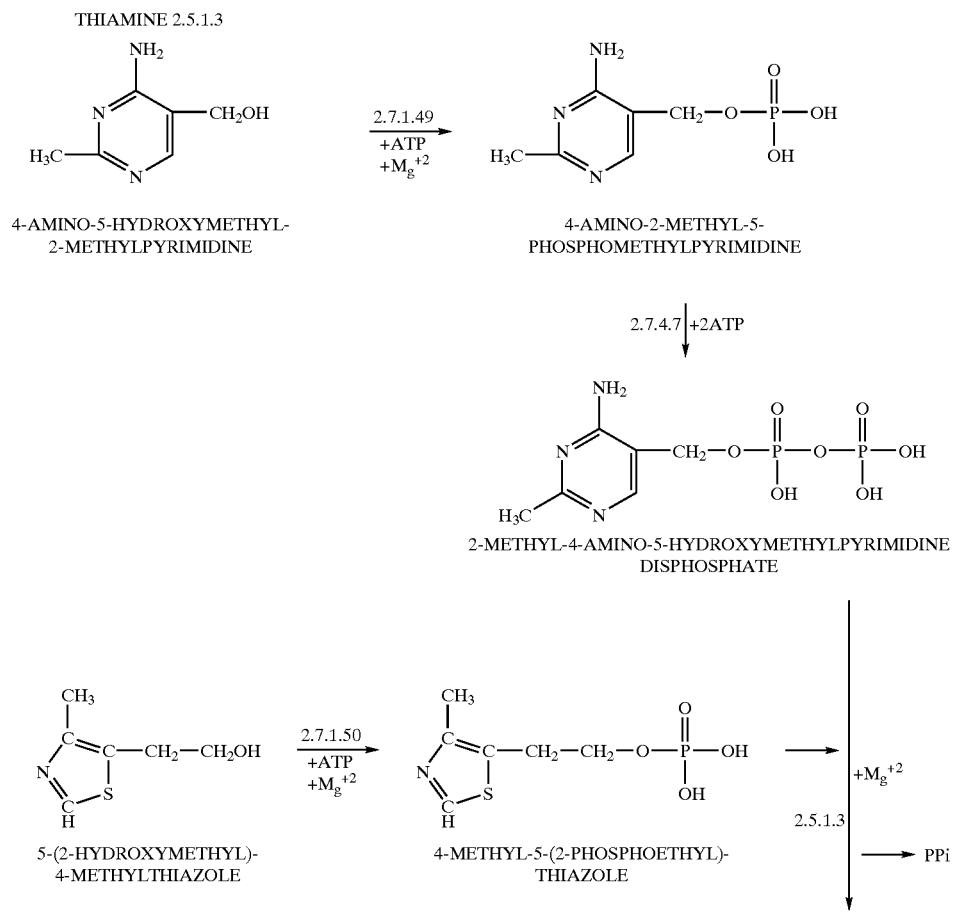

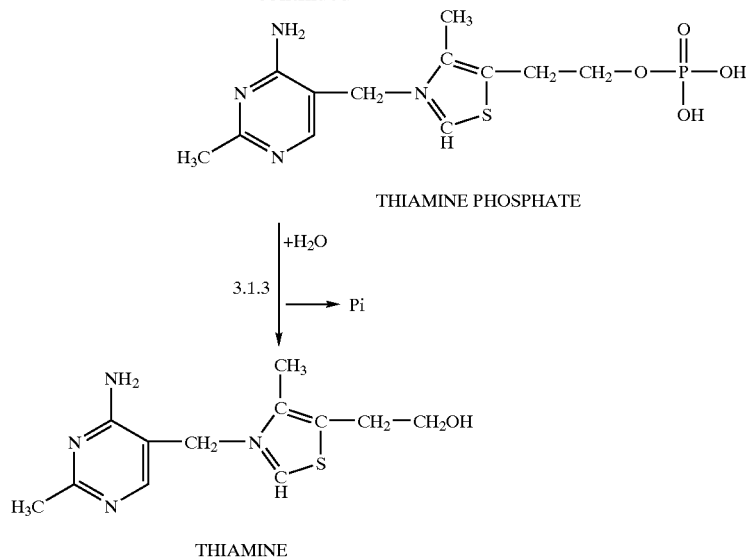

THIAMINE PHOSPHATE

THIAMINE

As noted above, in bacteria and fungi, phosphomethylpyrimidine kinase; (EC 2.7.4.7) catalyzes the reaction of ATP+4-amino-2-methyl-5-phosphomethylpyrimidine to produce ADP+4-amino-2-methyl-5-diphosphomethylpyrimidine; thiamine-phosphate diphosphorylase; (EC 2.5.1.3) catalyzes the reaction of 2-methyl-4-amino-5-hydroxymethylpyrimidine diphosphate+4-methyl-5-(2-phosphono-oxyethyl)thiazole to produce diphosphate+thiamine monophosphate; (EC 3.1.3.-) catalyzes the reaction of thiamine monophosphate to produce thiamine. The present inventor has first recognized the importance of this distinction in providing a target for inhibition of pathogenic microorganisms.

As is well known, antibiotics are currently used to treat a wide range of bacterial and fungal infections, ranging from minor to life threatening infections. Broad spectrum antibiotics treat a variety of gram-positive and gram-negative bacteria and fungal organisms, while mild spectrum antibiotics only cover limited types of bacterial and fungal organisms and are useful for curing infections with known bacterial and fungal strains.

But it has recently been noted that pathogenic bacteria and fungi increasingly exhibit resistance to existing classes of antibiotics, such as penicillin, vancomycin and erythromycin. According to the Center for Disease Control, pathogenic resistance has significantly increased mortality rates, making infectious disease the third largest cause of death in the United States. The rates of antibiotic resistant bacteria have particularly increased recently with respect to *S. aureus, Enterococcus* strains, *S. pneumoniae* and *tuberculosis*.

The mechanism of action for most antibiotics is the inhibition of bacterial cell wall completion, or DNA or protein synthesis. Sulfonamides and trimethoprin act by inhibiting an essential metabolic step, namely folate synthesis. But there is a great need for new antibiotics with different targets, especially in light of the ever increasing problem of resistant strains.

The present inventor has found that compounds which act as inhibitors of any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-) offer another class of antibiotics which inhibit an essential metabolic step, namely a pathway essential for bacterial and fugal thiamine biosynthesis.

According to the present invention, an enzyme in a thiamine pathway which is important for continued growth and viability of a pathogenic microorganism but which is absent in humans provides a unique, specific target for compounds which can inhibit infections of such pathogenic microorganisms without causing undesirable side effects or toxicity to a mammalian patient. Various biosynthetic pathways have been identified in the literature for various microorganisms and for mammals, and those pathways, which include an important enzyme present in pathogenic microorganisms but absent in mammals, provide a unique target for screening for compounds useful for inhibiting pathogenic microorganism infections.

According to the present invention, the present inventor has specifically identified any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-) as an enzyme present in an important biosynthetic pathway for pathogenic microorganisms, but absent in mammals, specifically absent in humans. Since the biosynthetic pathway is important for thiamine biosynthesis in pathogenic microorganisms, inhibition of this pathway significantly decreases the viability of pathogenic microorganisms, leading ultimately to death of the microorganism, either by action of the inhibitor alone, or in combination with the patient's own immunological systems for resisting infections, or in combination with other antibiotics.

Although not considered a limiting list, the present inventor has specifically identified a number of important pathogenic bacterial and fungal microorganisms which require any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-), including, but not limited to *Yersinia pestis, Pseudomonas aeruginosa, Neisseria meningitides* serogroup A and B, *Helicobacter pylori, Streptococcus pneumoniae, Haemophilus influenzae, Mycobacterium leprae, Mycobacterium tuberculosis, Vibrio cholerae, Staphylococcus aureus*.

2. Description of Method for Inhibition Screening

As noted above, one aspect of the present invention is a method for the identification of a compound capable of inhibiting the growth of pathogenic microorganisms by interfering with the activity of any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-). Compounds can be identified by incubating a sample of bacteria in a solution containing a known amount of 4-amino-2-methyl-5-diphosphomethylpyrimidine; 2-methyl-4-amino-5-hydroxymethylpyrimidine diphosphate; thiamine monophosphate in the presence or absence of a test compound, assessing the effect on conversion of any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-) wherein, a lower level of conversion in the presence of the test compound, compared with the level of conversion in the absence of the test compound, indicates that the test compound inhibits the activity of the enzyme.

Compounds capable of inhibiting any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-) can also be identified by means of in vitro experiments by exposing a substrate comprising 4-amino-2-methyl-5-diphosphomethylpyrimidine; 2-methyl-4-amino-5-hydroxymethylpyrimidine diphosphate; thiamine monophosphate to a plurality of test compounds and identifying those compounds which inhibit the tested enzyme according to known catalytic measurement techniques.

One particular in vitro method for assessing the activity of an inhibitor to any of the last three enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-): Enzyme assays are performed at a subsaturating concentration of substrate (depending on the enzyme, 0.2–1 mM, 4-amino-2-methyl-5-diphosphomethylpyrimidine; 2-methyl-4-amino-5-hydroxymethylpyrimidine diphosphate; thiamine monophosphate=0.5 mM) under standard conditions in the absence and presence of the major activator for each enzyme (1–5 mM depending on enzyme). In this way, the effect of the inhibitors can be evaluated under the range of the expected in vivo conditions. Initial screening of a putative inhibitor typically includes testing at two concentrations (~25 μM and 1 mM)±major activator with appropriate controls and blanks for a total of 9 assays/inhibitor/enzyme (2 control assays—appropriate enzyme concentrations in the absence of inhibitor; 4 experimental assays; 1 blank in the absence of inhibitors; 2 blanks in the presence of inhibitor (no activator required).

3. Useful Inhibitors

Useful inhibitors can also be identified, and potential inhibitors assessed, by in vitro treatment of bacteria and fungi in, for example, culture tubes or Petri dish samples. Such assessments can be performed, for example, by spreading a measured aliquot of a diluted bacteria culture onto nutrient agar plates, both treated and control, and counting the number of visible cells. Detailed procedures are well known to those skilled in the art as shown for example in Miller, *Experiments in Molecular Genetics*, Cold Spring Harbor Laboratory, 1992.

For example, the effect of the test compound on the virulence of *H. influenzae* is assessed by comparing the survival rates of animals which have been administered the test compound with the survival rate of animals which have not been administered the test compound, wherein a higher survival rate of animal administered the test compound is an indication that the test compound has an effect on the virulence of *H. influenzae*.

To determine the effect of a test compound on colonization of the mucosal surface or on invasiveness and/or virulence of *H. influenzae*, the test compound is administered to the animals either prior to, at the time of, or after inoculation of the animals with *H. influenzae*. The test compound may be administered directly into the nasopharynx, or may be administered by any other route including any one of the traditional modes (e.g. orally, parentally, transdermally or transmuscosally), in a sustained, gels and liposomes, or rectally (e.g. by suppository or enema). Precise formulations and dosages will depend on the nature of the test compound and may be determined using standard techniques, by a pharmacologist of ordinary skill in the art.

Compounds which inhibit any of the enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-) can also be assessed in an animal model, an in vivo test. Such tests can be conducted in an animal which is susceptible to infection by the pathogenic microorganism of interest. In vivo animal model assessments can be conducted, for example, as in U.S. Pat. No. 5,871,951.

The present invention further provides a method for treating pathogenic microorganism infections in a patient by administering to the patient an effective amount of an inhibitor against any of the enzymes in the pathway, namely phosphomethylpyrimidine kinase; (EC 2.7.4.7), thiamine-phosphate diphosphorylase; (EC 2.5.1.3), and phosphohistidine phosphatase; (EC 3.1.3.-),wherein an effective amount of the inhibitor will inhibit the activity of the enzyme so as to decrease viability of and/or kill the microorganism. The inhibitor utilized in the treatment may be one identified by one of the methods described above, or inhibitors may be identified by any other method. Inhibitors of phosphomethylpyrimidine kinase; (EC 2.7.4.7), thiamine-phosphate diphosphorylase; (EC 2.5.1.3), and phosphohistidine phosphatase; (EC 3.1.3.-) have the following structures:

Exemplary Inhibitors of phosphomethylpyrimidine kinase (EC 2.7.4.7) are the following:

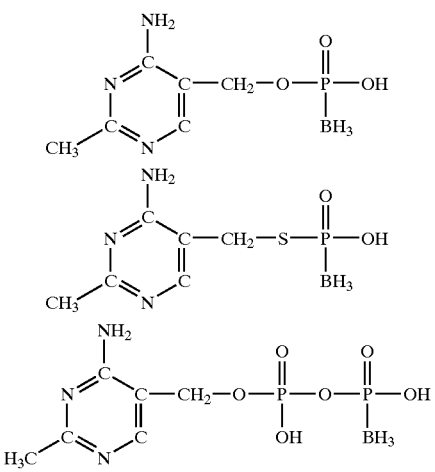

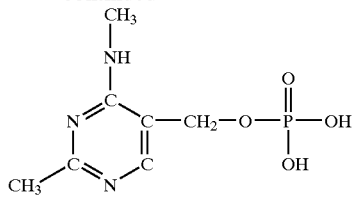

Exemplary inhibitors of thiamine-phosphate diphosphorylase (EC 2.5.1.3) are:

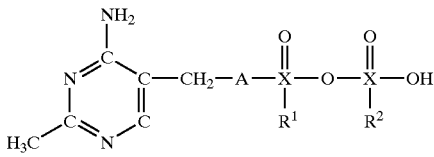

wherein at least one of $R^1$ and $R^2$ is $BH_3$, X is P or S, and A is O or S.

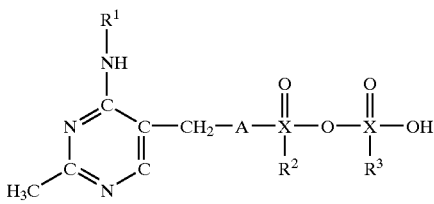

wherein $R^1$ is H or $C_{1-5}$ alkyl, $R^2$ and $R^3$ are each OH or $BH_3$, X is P or S, and A is O or S.

Exemplary inhibitors of phosphohistidine phosphatase have the following structure:

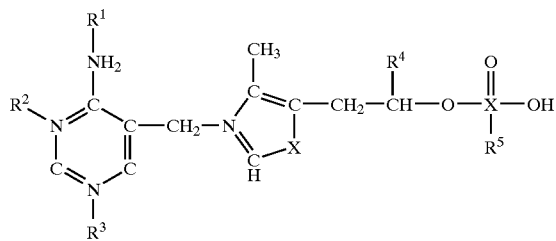

wherein $R^1$ is H or $CH_3$, $-CH_2CH_3$, $-CH_2CH_2CH_3$ or $CH_2CH_2CH_2CH_3$, $R^2$ is nothing or is $CH_3$, $-CH_2CH_3$, $-CH_2CH_2CH_3$ or $CH_2CH_2CH_2CH_3$ replacing the double-bond to the N, R3 is nothing or is CH3, $-CH_2CH_3$, $-CH_2CH_2CH_3$ or $CH_2CH_2CH_2CH_3$ replacing the double-bond to the N, R4 is H, SH or $C_{1-5}$alkyl, X is P or S and $R^5$ is OH, SH, or $C_{1-5}$alkyl.

Particular examples are (a) the compound wherein X is S; (b) the compound wherein X is P and $R^5$ is SH; (c) the compound wherein $R^1$ is $CH_3$ and (d) the compound wherein $R^4$ is SH.

The above compounds can be prepared by those skilled in the art by known procedures for derivatizing the substrate compound in the pathway.

Pharmaceutical Administration

Inhibitors useful for the treatment of pathogenic bacteria and microorganisms can be administered by a variety of means and dosage forms well known to those skilled in the art. When used as an antimicrobial agent in the treatment of microorganism infections, the present compounds are administered, for example, orally in the form of a tablet, capsule, powder, syrup, etc., or parenterally such as intravenous injection, intramuscular injection, or intrarectal administration.

The suitable administration forms as mentioned above may be prepared by mixing an active ingredient with a conventional pharmaceutically acceptable carrier, excipient, binder, stabilizer, etc. When administered in the form of an injection, a pharmaceutically acceptable buffering agent, solubilizer, isotonic agent, etc. may be added thereto. The active compound may be administered per se, or in the form of a pharmaceutically acceptable salt thereof, or in the form of a pro-drug, such as an ester.

The dosage of the compound varies according to the conditions, ages, weights of the patient, the administration form, the frequency of the administration, etc., but it is usually in the range of 100 to 3000 mg per day for an adult, which is administered once or divided into several dosage units.

All of the publications referred to herein, are hereby specifically incorporated by reference.

The following provisional applications are hereby incorporated by reference:

| Attorney Docket No. | Serial No. | Filing Date |
|---|---|---|
| 3781-0110P | 60/357,222 | Feb. 14, 2002 |
| 3781-0111P | 60/372,459 | Apr. 11, 2002 |
| 3781-0112P | 60/371,670 | Apr. 10, 2002 |
| 3781-0113P | 60/368,738 | Mar. 27, 2002 |
| 3781-0114P | 60/368,614 | Mar. 27, 2002 |
| 3781-0115P | 60/372,478 | Apr. 15, 2002 |
| 3781-0116P | 60/372,307 | Apr. 12, 2002 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for identifying a therapeutically active compound that affects the viability or infectivity of a pathogenic microorganism which comprises:
   a) identifying a metabolic pathway in a pathogenic microorganism that is essential to the viability or infectivity of said microorganism;
   b) identifying an enzyme in said pathway which enzyme is not present in mammals;
   c) confirming that said enzyme is a valid target for affecting the viability or infectivity of said microorganism; and
   d) identifying a compound that inhibits said enzyme.

2. The method according to claim 1, wherein said pathway is a pathway involved in energy production or metabolism in said microorganism.

3. The method according to claim 1, wherein said enzyme is identified by comparing the components of said pathway in humans to the components of said pathway in pathogenic microorganisms, and thereby identifying an enzyme in said pathway that is not present in humans.

4. The method according to claim 1, wherein said enzyme is confirmed as a valid therapeutic target by producing a genetically transformed version of said microorganism wherein the gene which codes for said enzyme is not present or is not capable of producing a normal functioning enzyme and culturing said genetically transformed microorganism.

5. The method according to claim 4, wherein a genetically transformed version of said microorganism is produced wherein the gene for said enzyme is mutated in the coding region for said enzyme, whereby said genetically transformed microorganism is not capable of producing said enzyme.

6. The method according to claim 4, wherein said transformed microorganism is cultured under conditions sufficient for growth of the wild type microorganism and assessing the viability and/or infectivity of said transformed microorganism.

7. The method according to claim 1, wherein a compound is tested for in vitro inhibition against said enzyme.

8. The method according to claim 7, wherein a compound active for in vitro inhibition against said enzyme is tested for in vivo or ex vivo activity against said pathogenic microorganism.

9. The method according to claim 7, wherein a compound active for in vitro inhibition of said enzyme is tested for inhibiting the growth or virulence of said pathogenic microorganism in culture.

10. The method according to claim 9, wherein a compound active for inhibiting the growth of said pathogenic microorganism in culture is tested for activity to inhibit the viablility or infectivity of said pathogenic microorganism in a mammal.

11. A method for identifying a therapeutically active compound that affects the viability or infectivity of a pathogenic microorganism which comprises:

a) identifying a metabolic pathway in a pathogenic microorganism that is essential to the viability and/or infectivity of said microorganism;

b) identifying an enzyme in said pathway which enzyme is not present in humans;

c) confirming that said enzyme is a valid therapeutic target by producing a genetically transformed version of said microorganism wherein the gene which codes for said enzyme is not present or is not capable of producing a normal functioning enzyme and culturing said genetically transformed microorganism;

d) identifying a compound which inhibits the in vitro activity of said enzyme; and e) testing said compound for in vivo or ex vivo therapeutic activity against said microorganism to confirm the ability of said compound to affect the viability or infectivity of said pathogenic microorganism.

12. The method according to any one of claims 1–11, wherein said pathogenic microorganism is a bacteria, protists, yeast or fungi.

13. The method according to claim 12, wherein said microorganism is a member selected from the group consisting of *Yersinia pestis, Pseudomonas aeruginosa, Neisseria meningitides* serogroup A and B, *Helicobacter pylori, Chlamydia trachomatis, Chlamydia pneumoniae, Streptococcus pneumoniae, Haemophilus influenzae, Mycobacterium leprae, Mycobacterium tuberculosis, Vibrio cholerae, Staphylococcus aureus, Giardia lamblia, Entamoeba histolytica, Trichomonas vaginalis, Leishmania donovani, Trypannosome cruzi, Candida albicans,* and *Plasmodium falciparum.*

* * * * *